(12) United States Patent
Valeti et al.

(10) Patent No.: US 9,943,665 B2
(45) Date of Patent: Apr. 17, 2018

(54) ATRAUMATIC MEDICAL DEVICE

(71) Applicant: MedWerks, LLC, St. Paul, MN (US)

(72) Inventors: Uma S. Valeti, St. Paul, MN (US);
Robert F. Wilson, Roseville, MN (US);
John P. Gainor, Mendota Heights, MN (US)

(73) Assignee: MedWerks, LLC, St. Paul, MN (US)

( * ) Notice: Subject to any disclaimer, the term of this patent is extended or adjusted under 35 U.S.C. 154(b) by 0 days.

(21) Appl. No.: 14/516,526

(22) Filed: Oct. 16, 2014

(65) Prior Publication Data

US 2015/0105729 A1    Apr. 16, 2015

Related U.S. Application Data

(60) Provisional application No. 61/891,797, filed on Oct. 16, 2013.

(51) Int. Cl.
| | |
|---|---|
| *A61M 25/00* | (2006.01) |
| *A61N 1/05* | (2006.01) |
| *A61B 18/14* | (2006.01) |
| *A61B 18/02* | (2006.01) |
| *A61B 18/00* | (2006.01) |
| *A61B 90/00* | (2016.01) |

(52) U.S. Cl.
CPC ....... *A61M 25/008* (2013.01); *A61B 18/1492* (2013.01); *A61M 25/0074* (2013.01); *A61N 1/0565* (2013.01); *A61B 18/02* (2013.01); *A61B 2018/00113* (2013.01); *A61B 2018/00196* (2013.01); *A61B 2018/00351* (2013.01); *A61B 2018/00577* (2013.01); *A61B 2018/1465* (2013.01); *A61B 2090/065* (2016.02); *A61B 2090/3784* (2016.02); *A61M 2025/0081* (2013.01)

(58) Field of Classification Search
CPC . A61B 18/1492; A61B 5/6839; A61B 5/6882; A61B 17/04; A61M 25/0068; A61N 1/0558
See application file for complete search history.

(56) References Cited

U.S. PATENT DOCUMENTS

| | | | |
|---|---|---|---|
| 5,192,290 A | 3/1993 | Hilal | |
| 5,429,131 A | 7/1995 | Scheinman et al. | |
| 7,311,704 B2 | 12/2007 | Paul et al. | |
| 2005/0267332 A1* | 12/2005 | Paul .............. | A61B 18/1492 600/127 |
| 2007/0219466 A1 | 9/2007 | Tremulis et al. | |

(Continued)

OTHER PUBLICATIONS

WIPO, U.S. International Search Authority, International Search Report and Written Opinion dated Jan. 29, 2015 in International Patent Application No. PCT/US2014/060976, 8 pages.

*Primary Examiner* — Christopher D Koharski
*Assistant Examiner* — Natasha Patel
(74) *Attorney, Agent, or Firm* — Inskeep IP Group, Inc.

(57) ABSTRACT

A catheter with a spring tip that facilitates atraumatic initial placement and also continues to protect tissue contacted by the catheter device subsequent to the initial placement. The spring tip is shock-absorbing and axially compliant and allows enhanced use of various devices in conjunction with the tip such as bioptomes, electrodes, needles, flushing catheters, delivery catheters, and the like. The atraumatic shock-absorbing tip could include conductive or non-conductive materials.

13 Claims, 31 Drawing Sheets

(56) References Cited

U.S. PATENT DOCUMENTS

| | | |
|---|---|---|
| 2009/0093806 A1 | 4/2009 | Govari et al. |
| 2009/0216221 A1* | 8/2009 | Davis ................ A61B 18/1492 606/33 |
| 2009/0312834 A1* | 12/2009 | Wood ........................ A61F 2/90 623/1.44 |
| 2010/0145306 A1* | 6/2010 | Mickley ............. A61B 17/3478 604/508 |
| 2011/0137399 A1 | 6/2011 | Chomas et al. |
| 2011/0184406 A1 | 7/2011 | Selkee |

\* cited by examiner

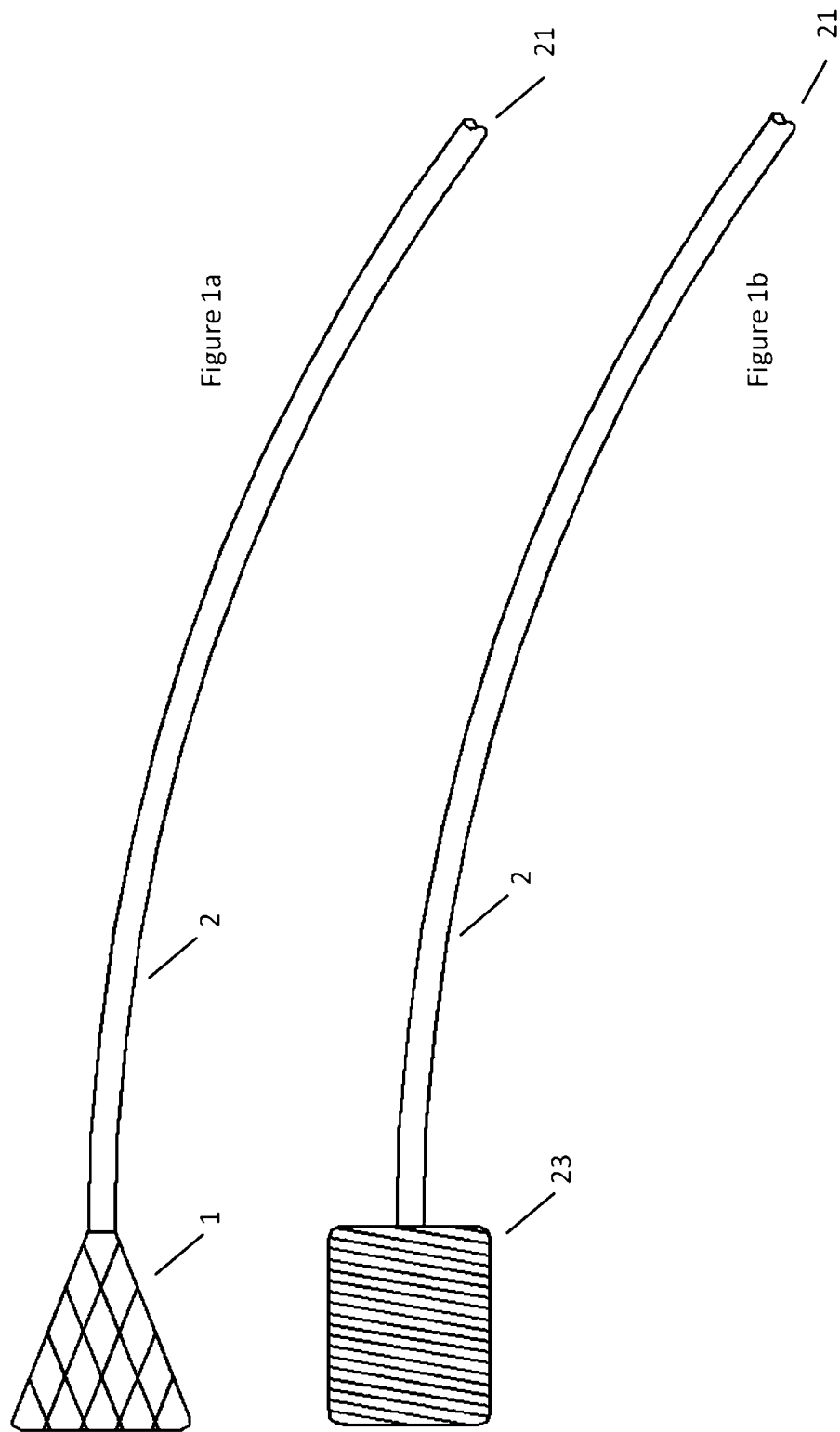

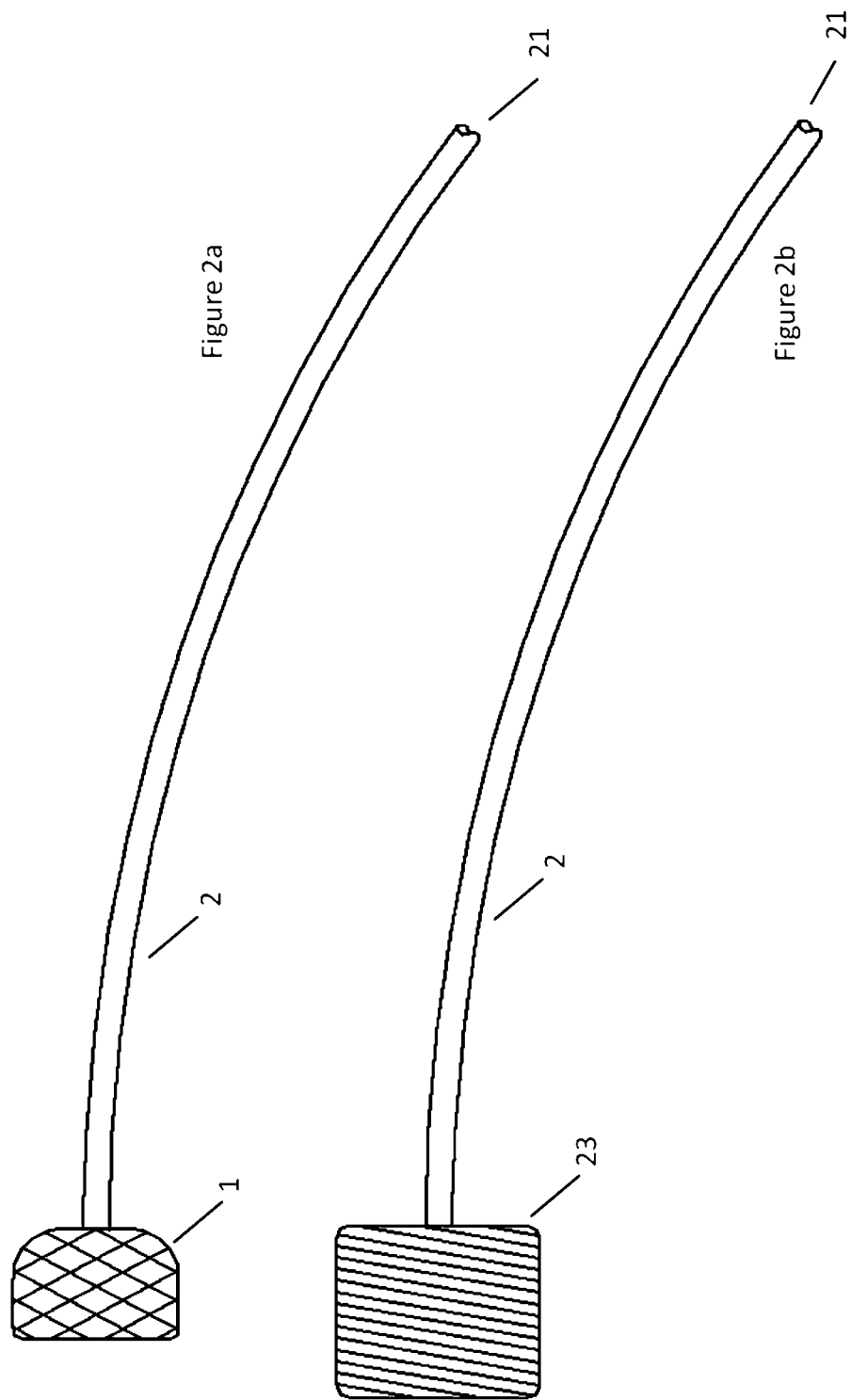

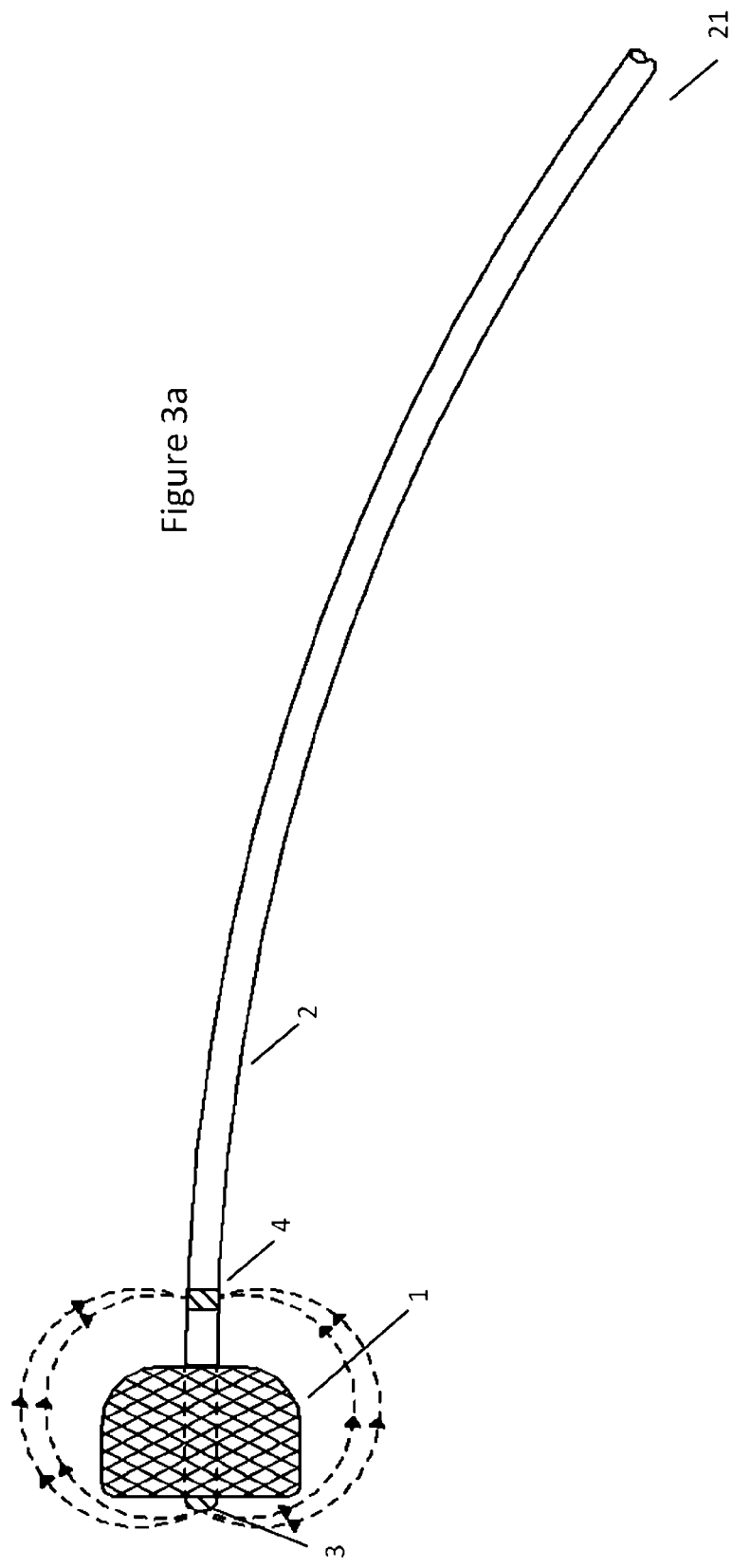

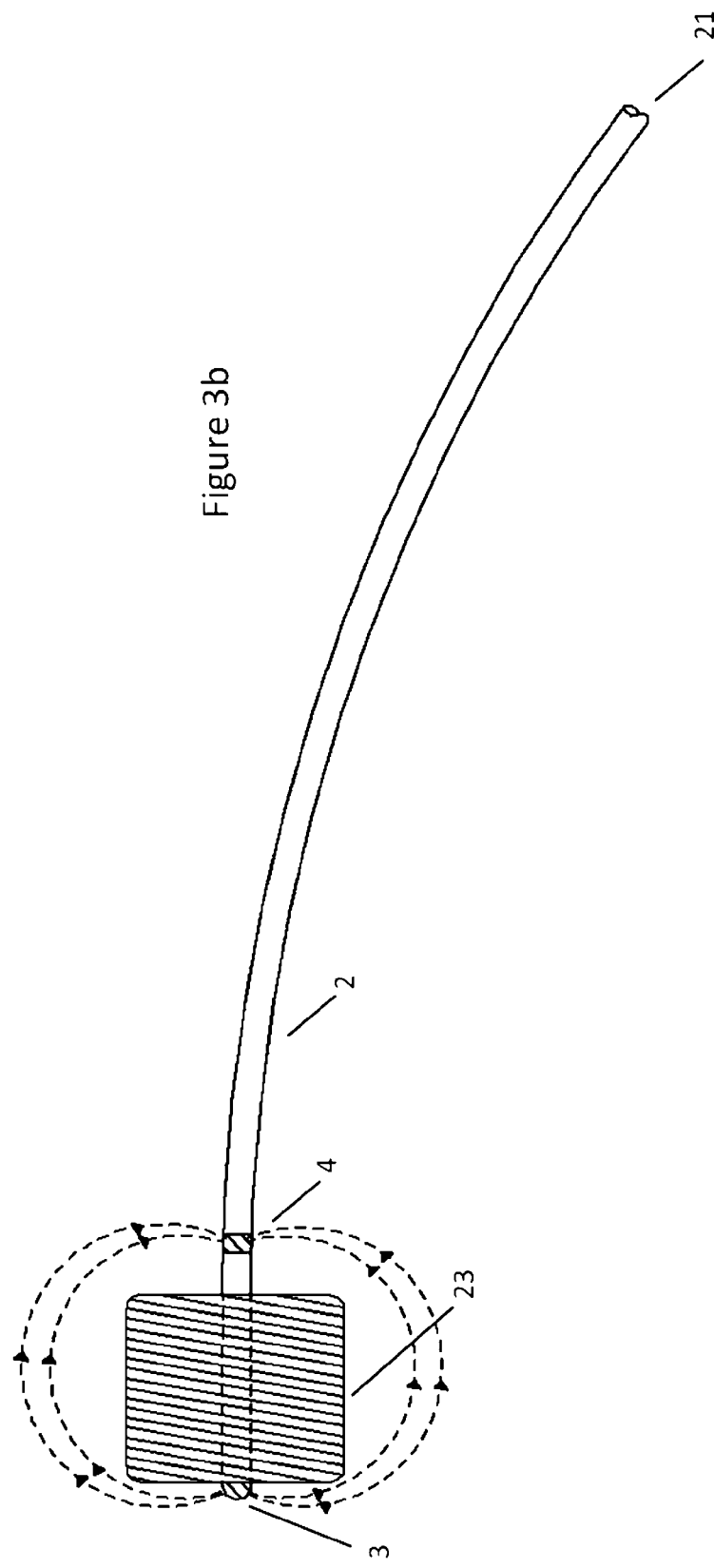

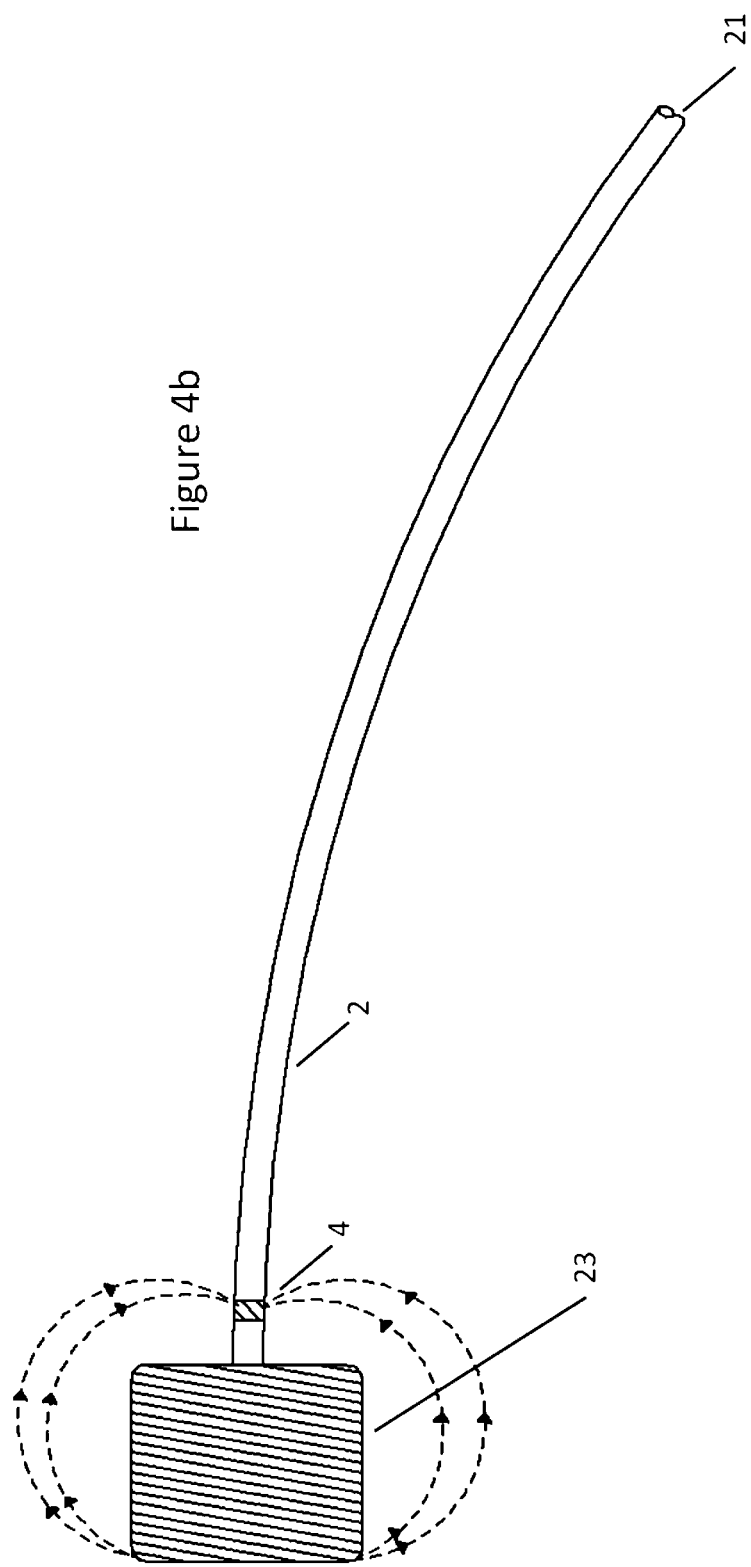

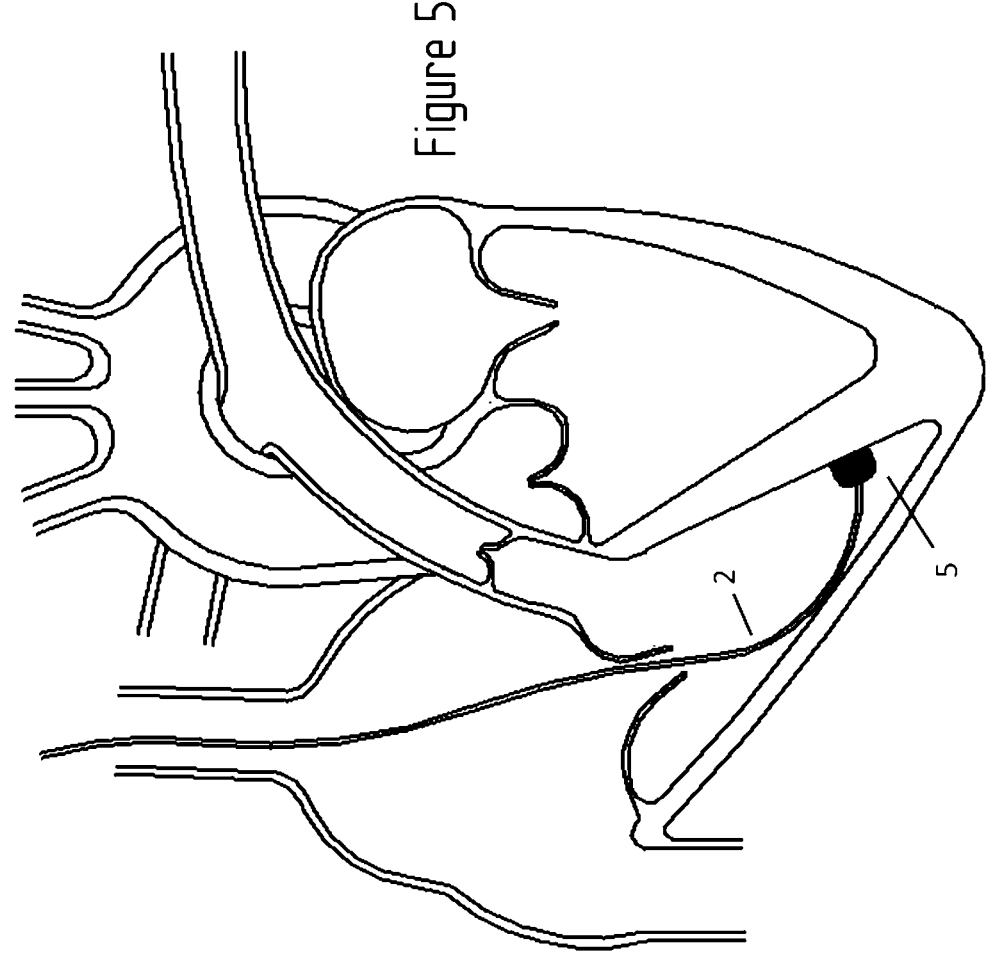

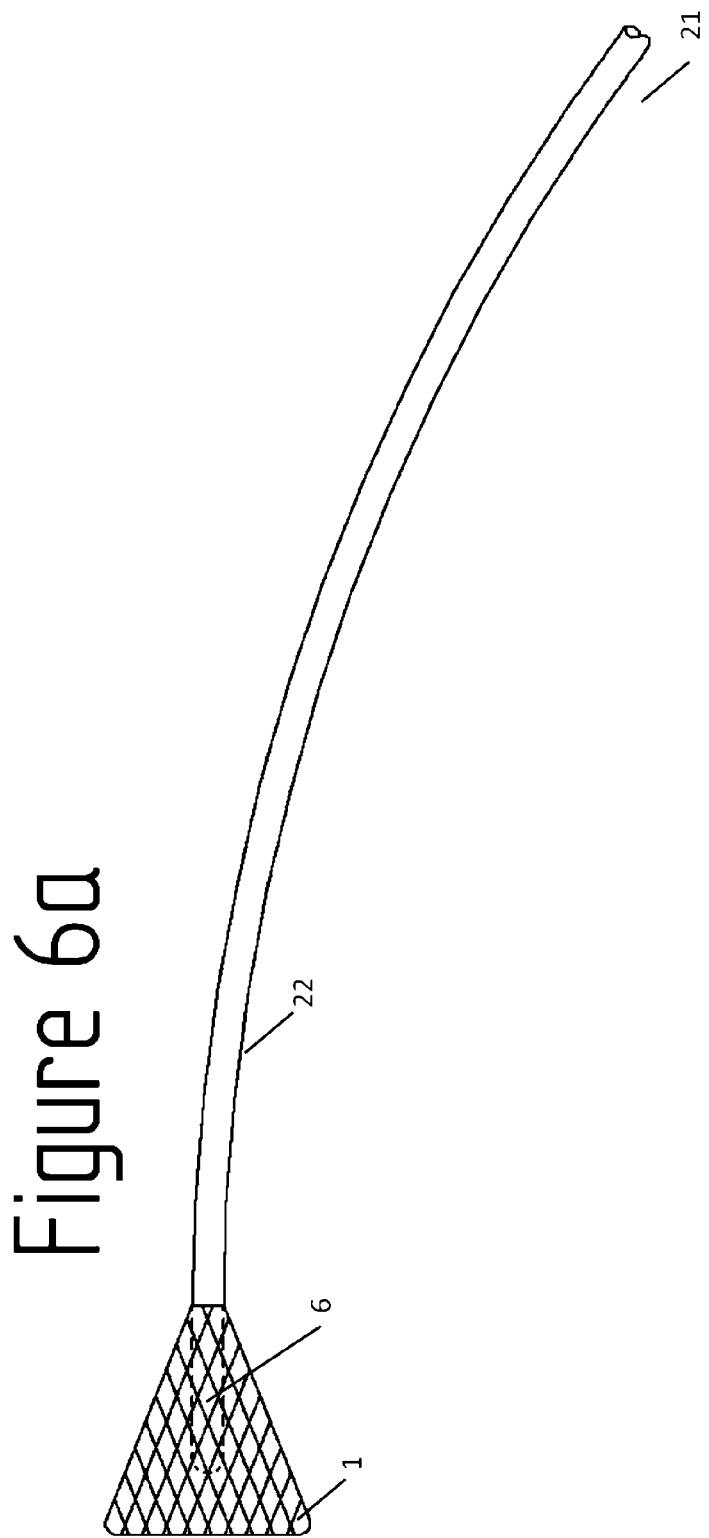

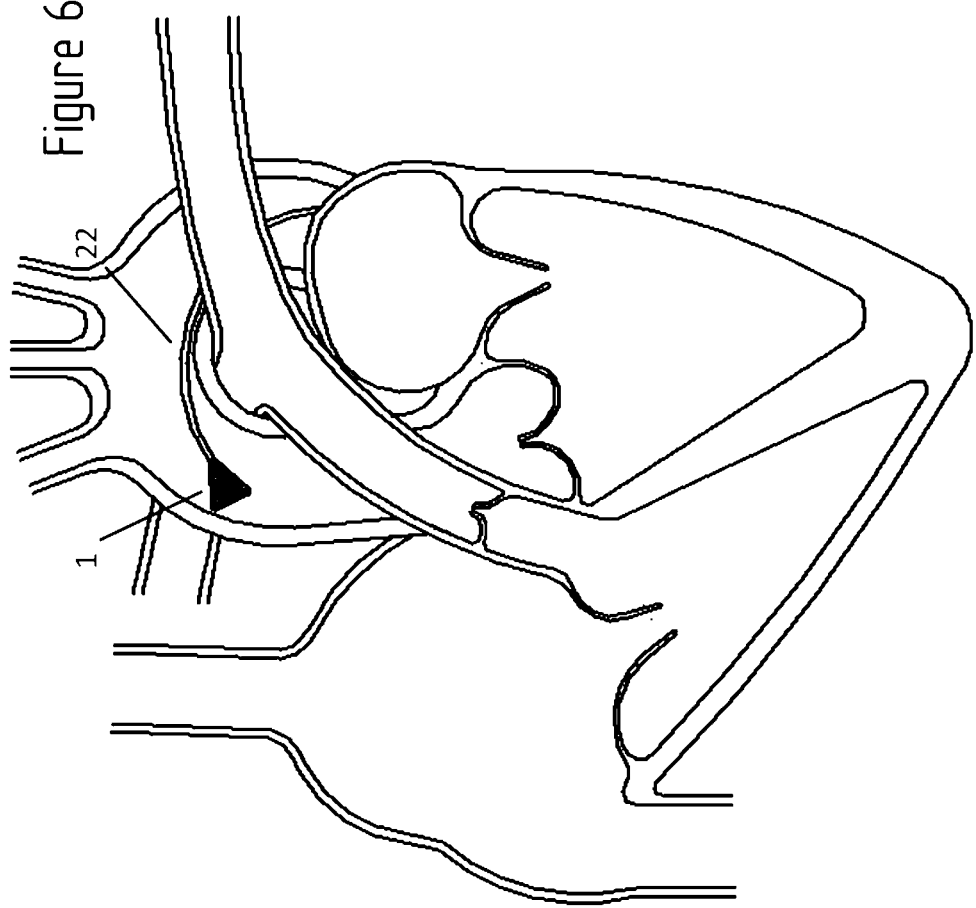

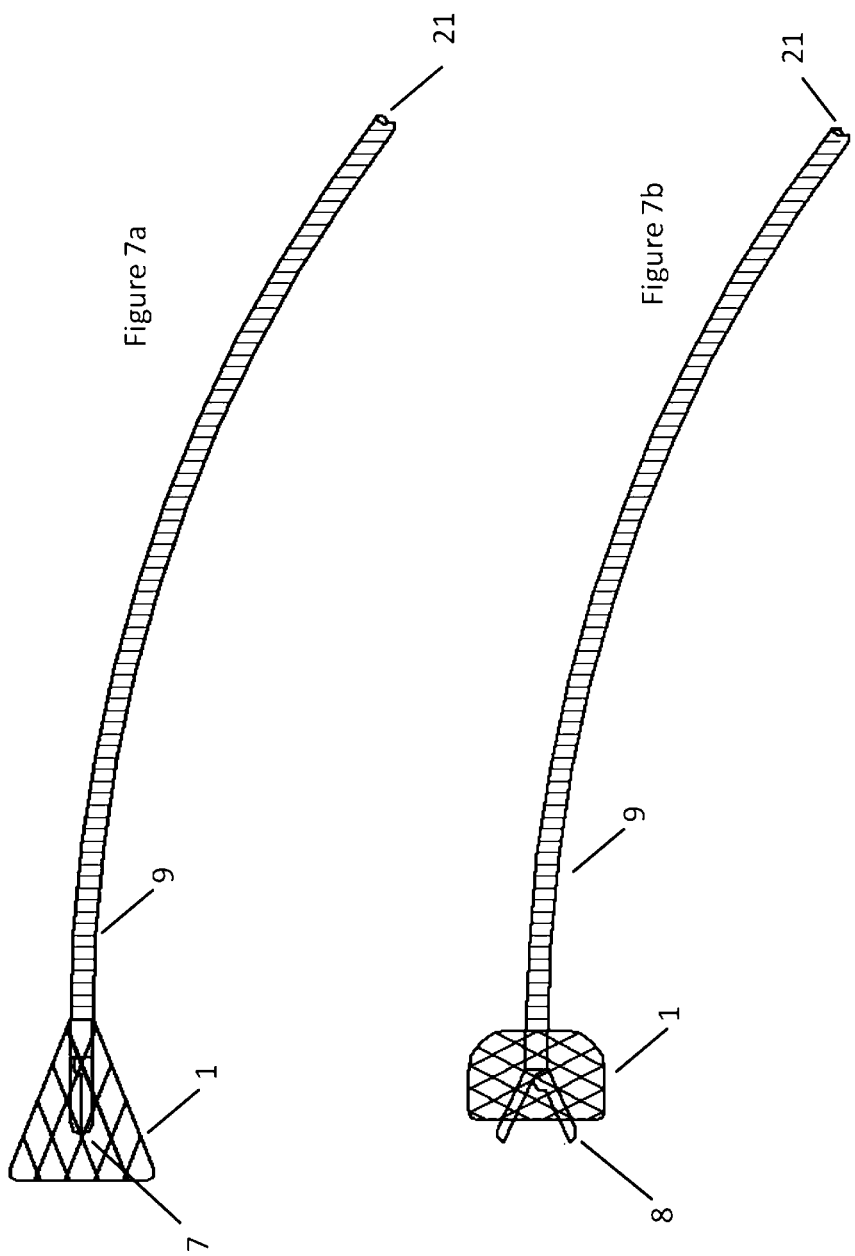

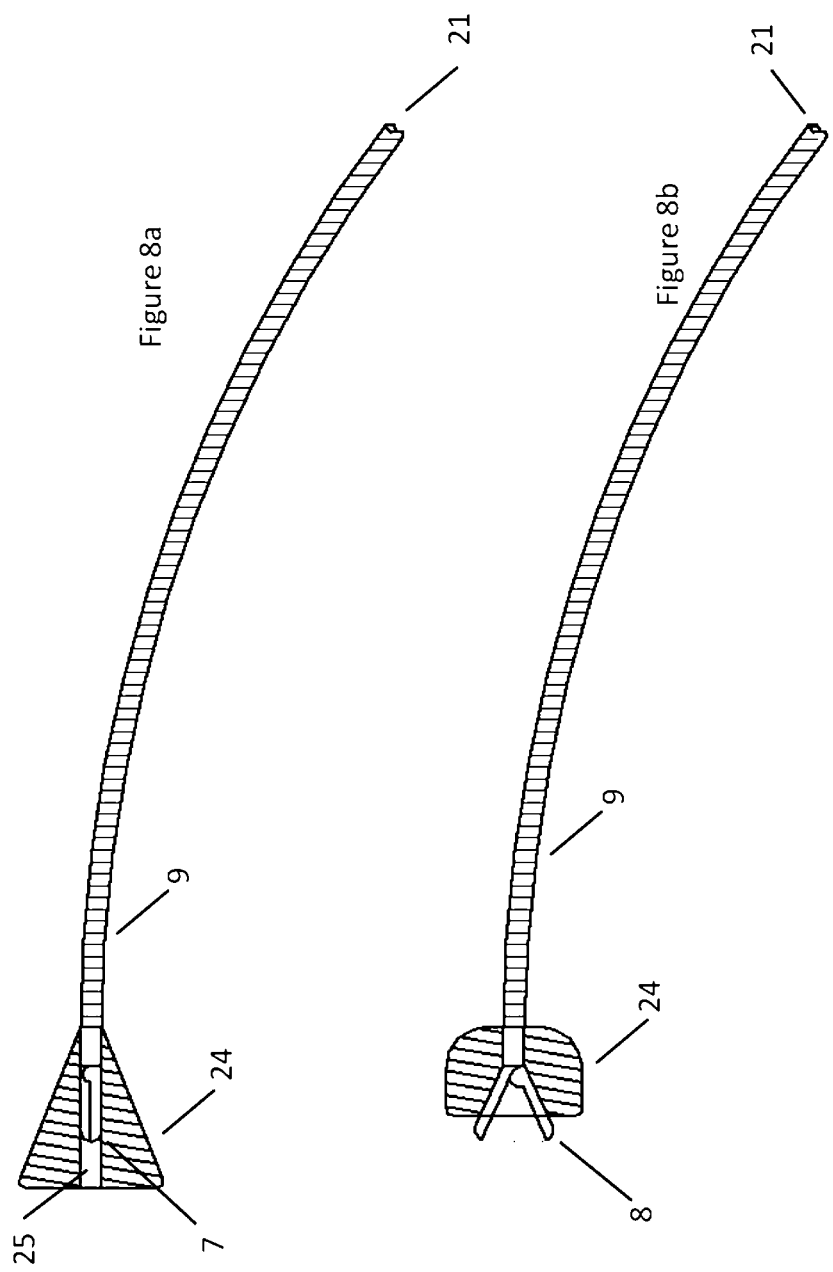

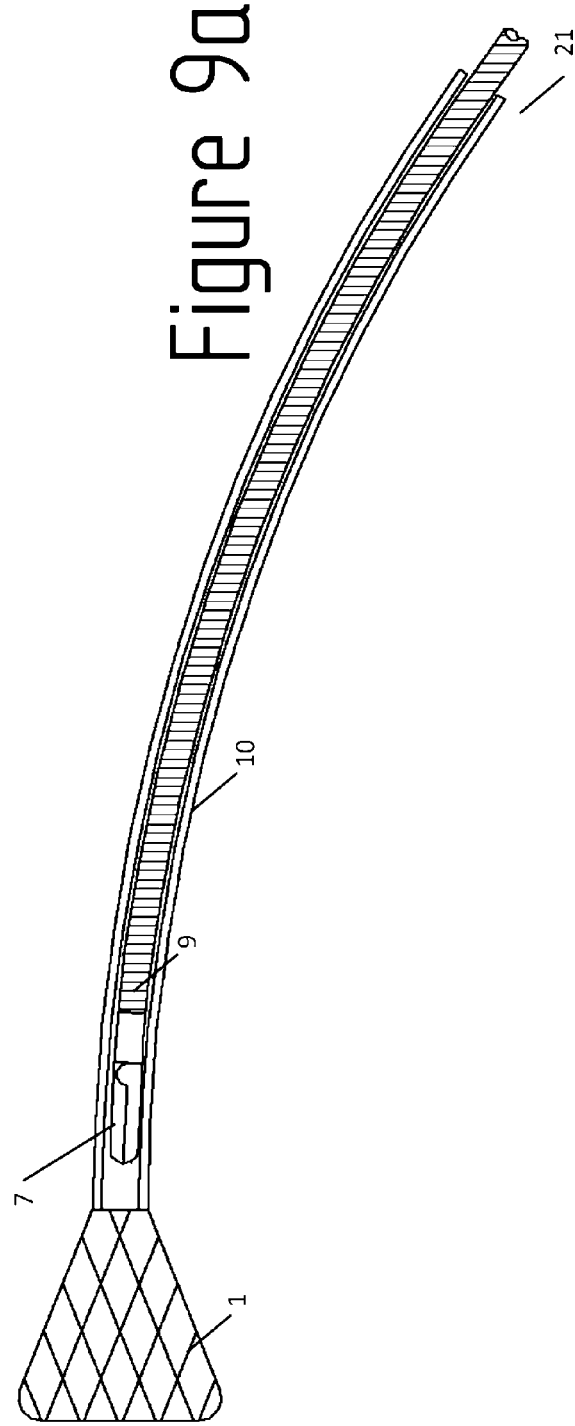

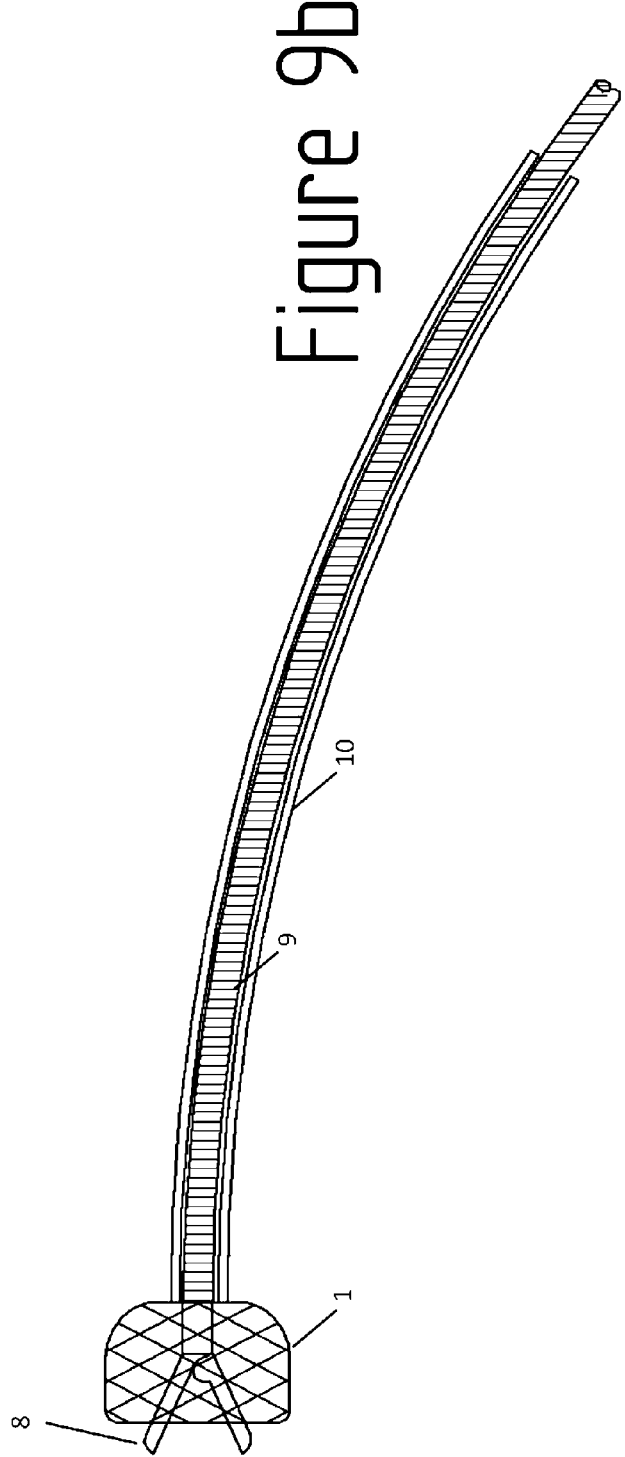

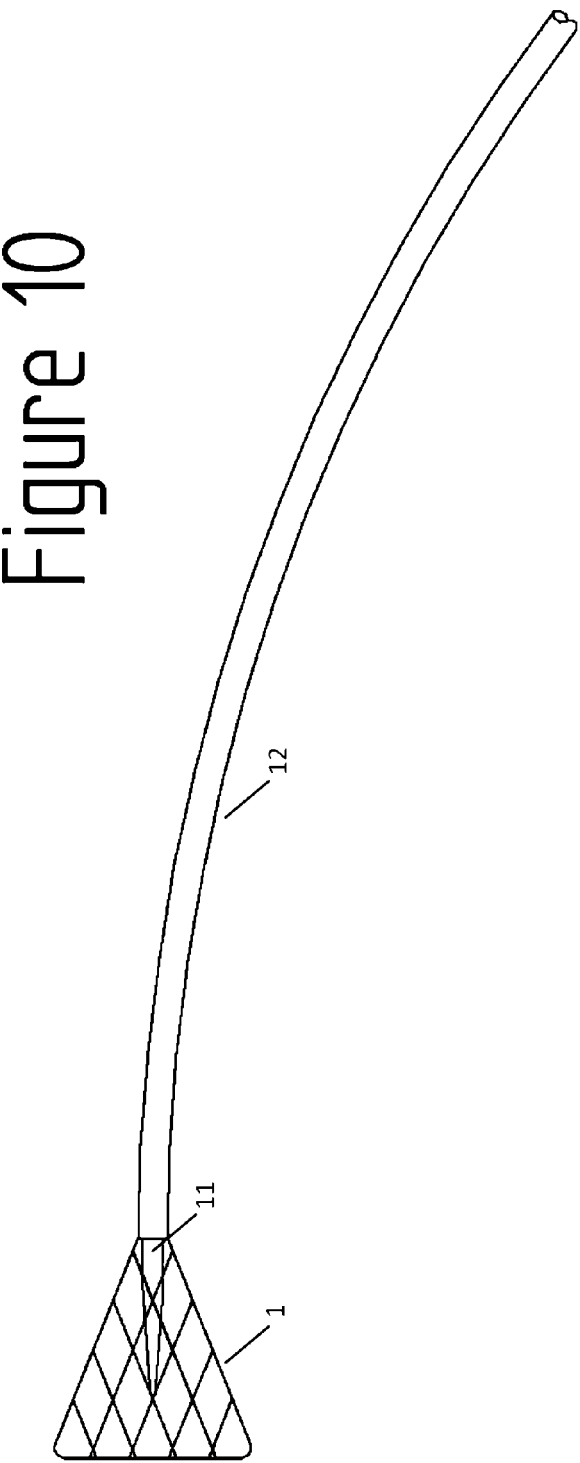

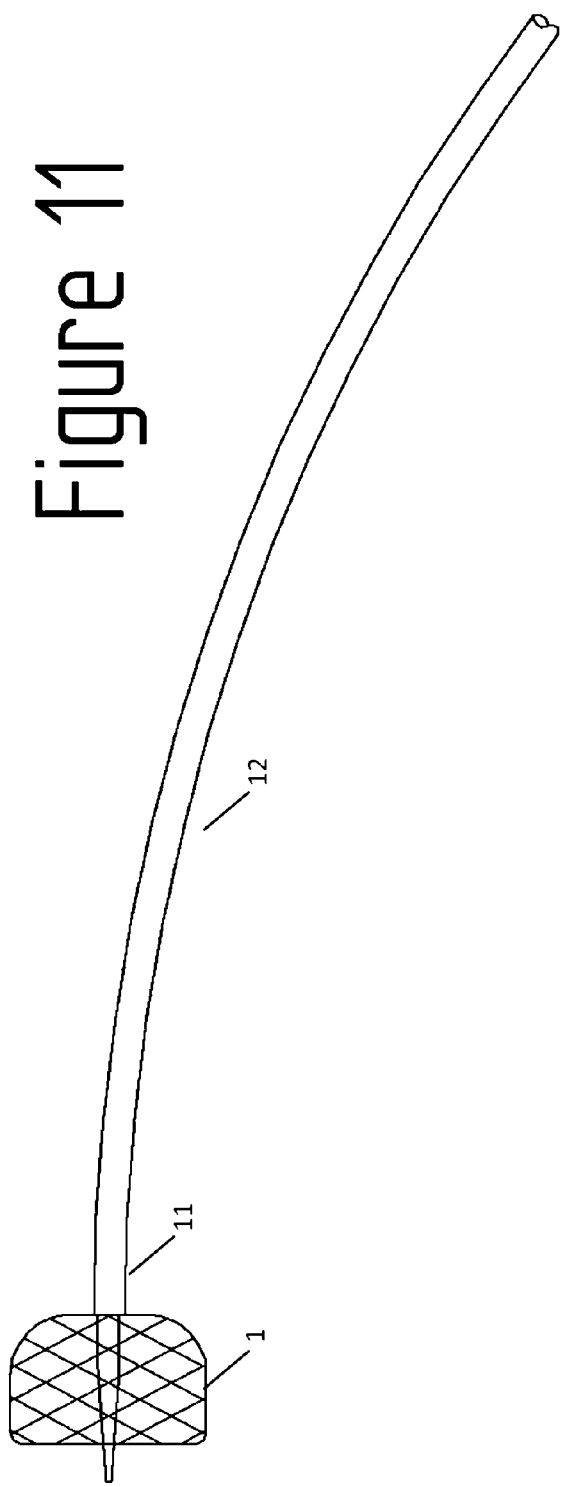

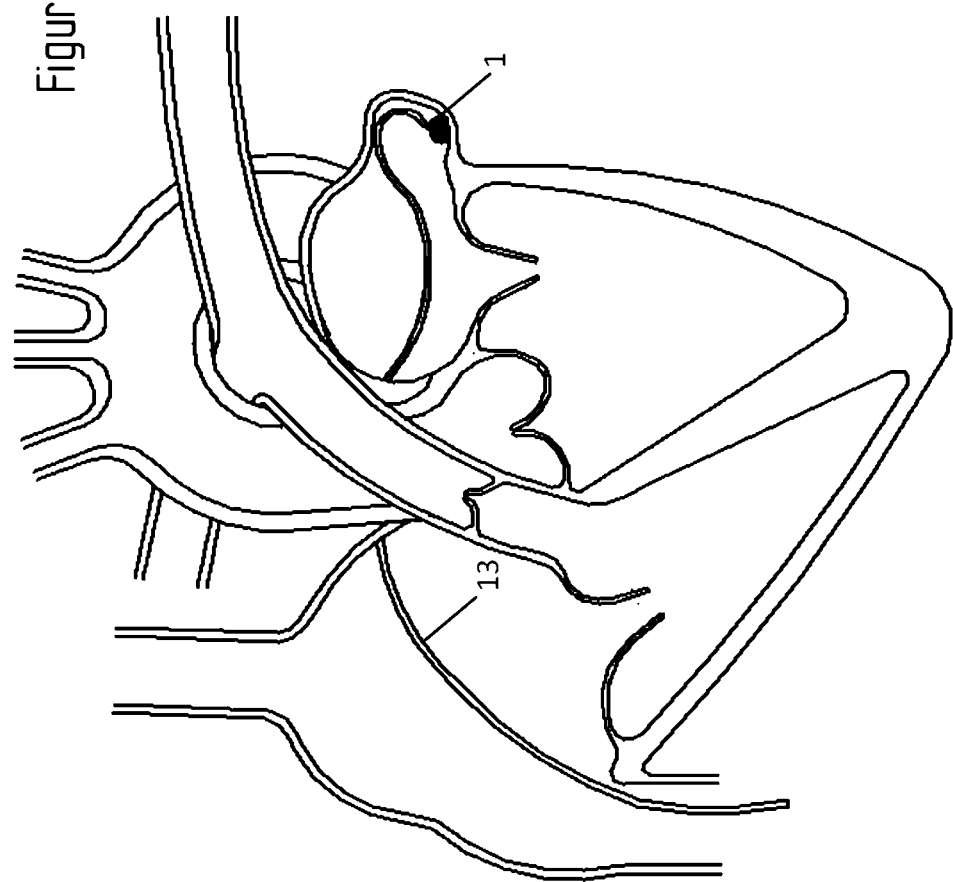

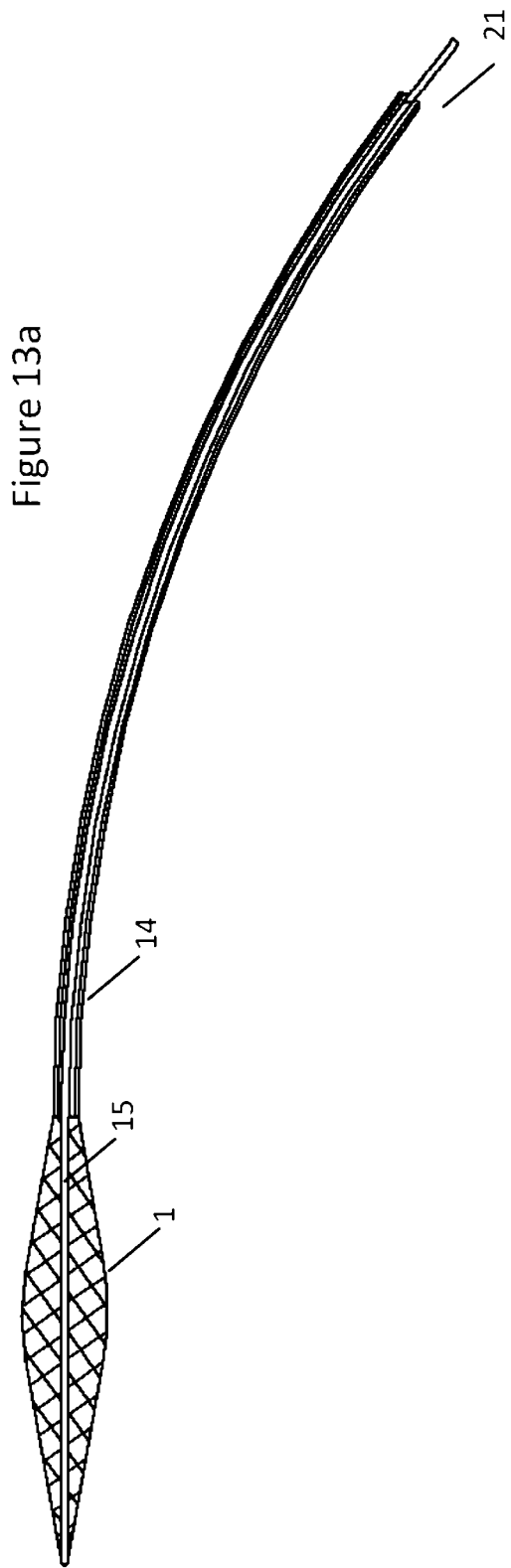

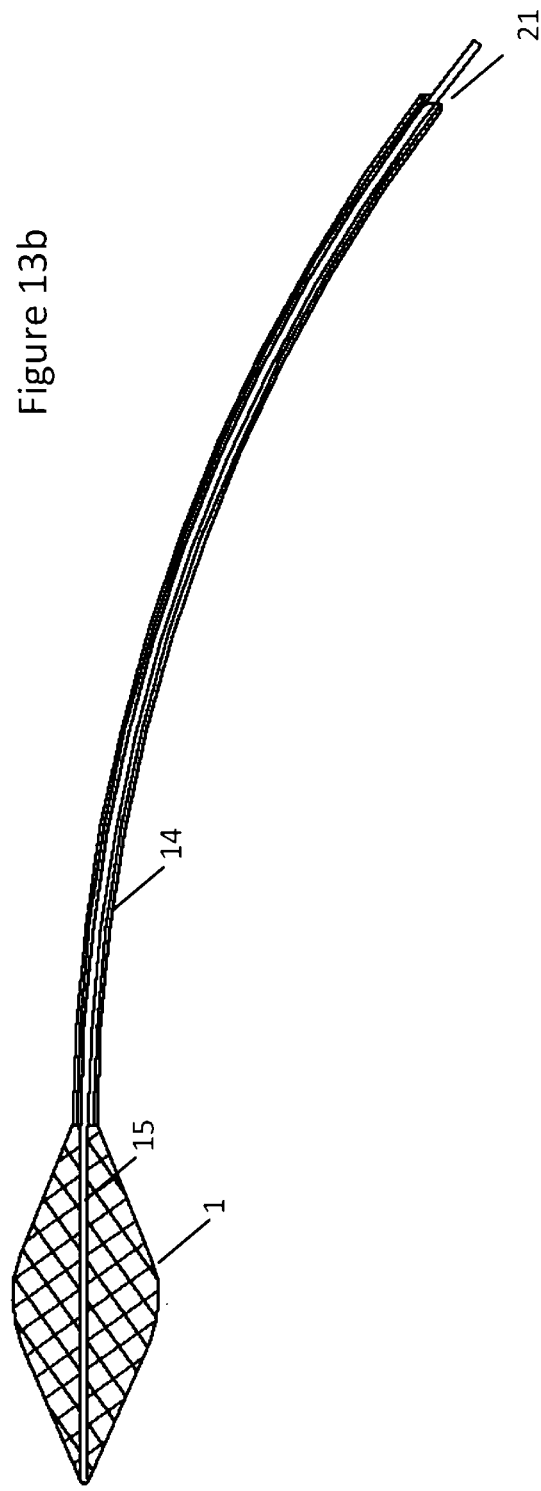

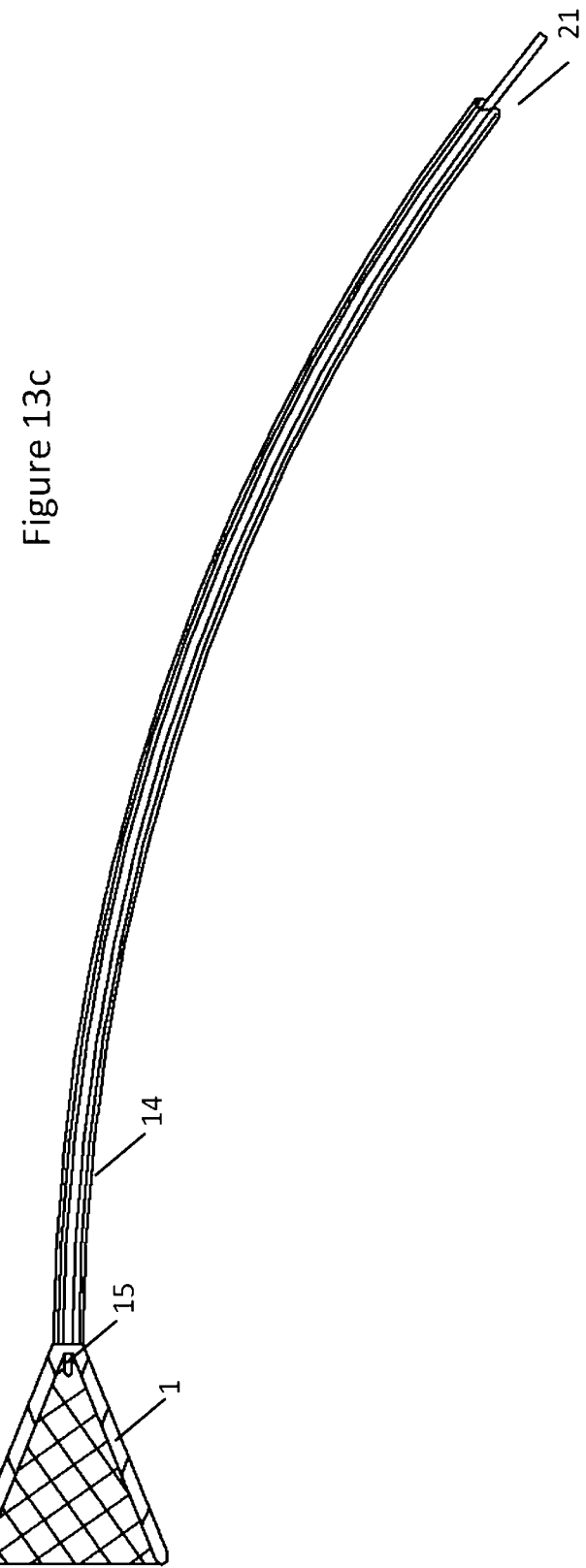

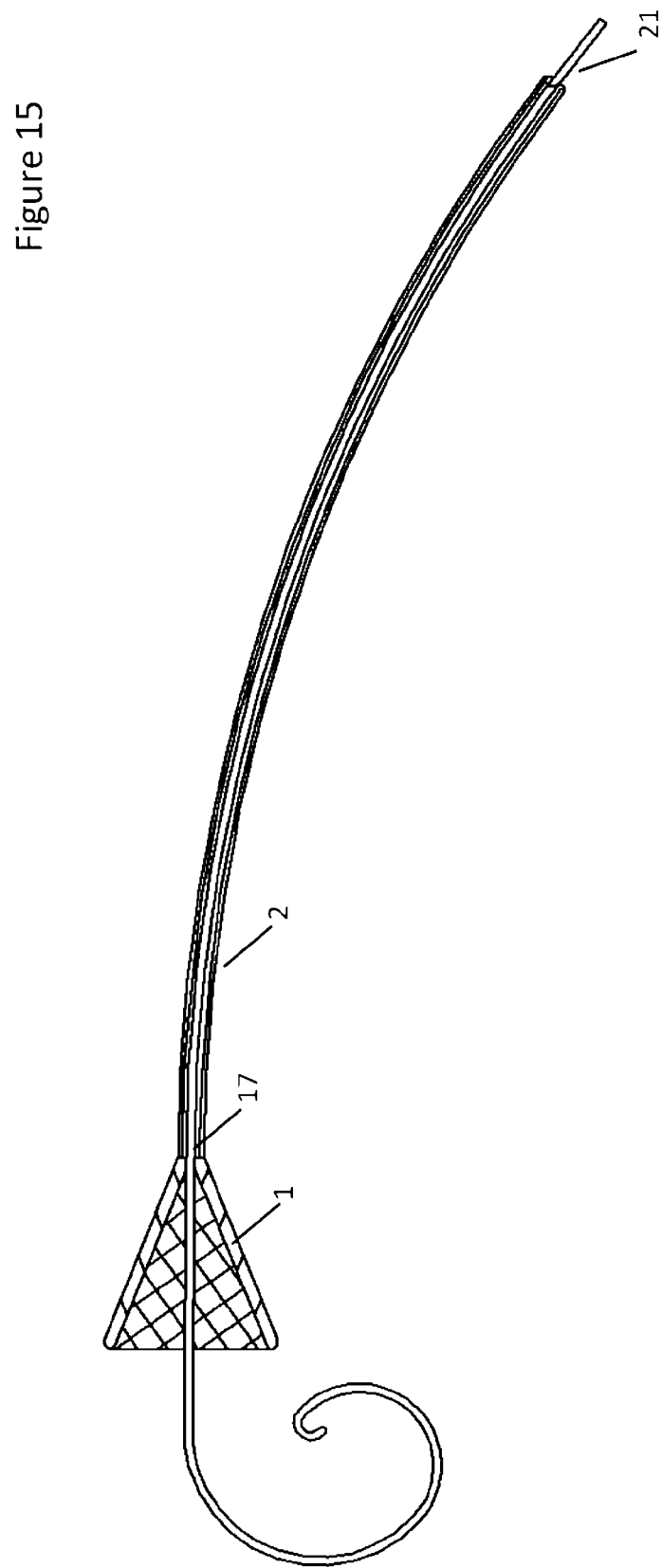

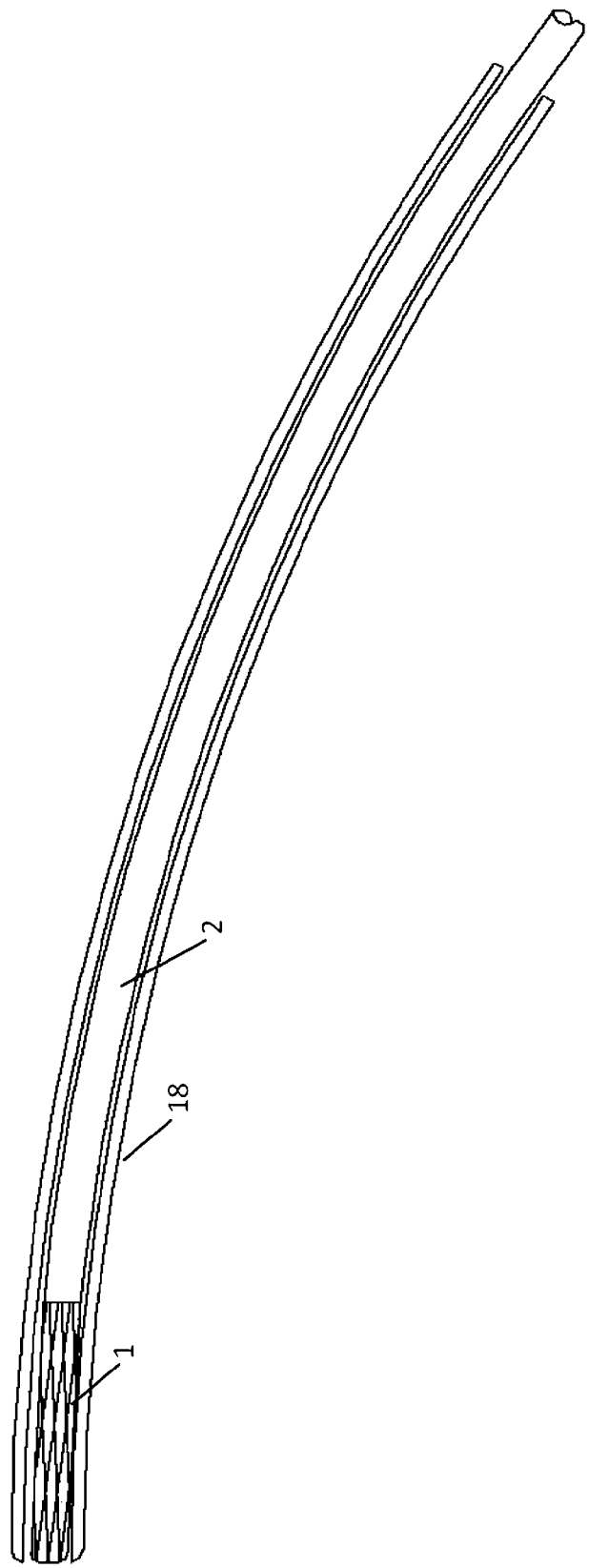

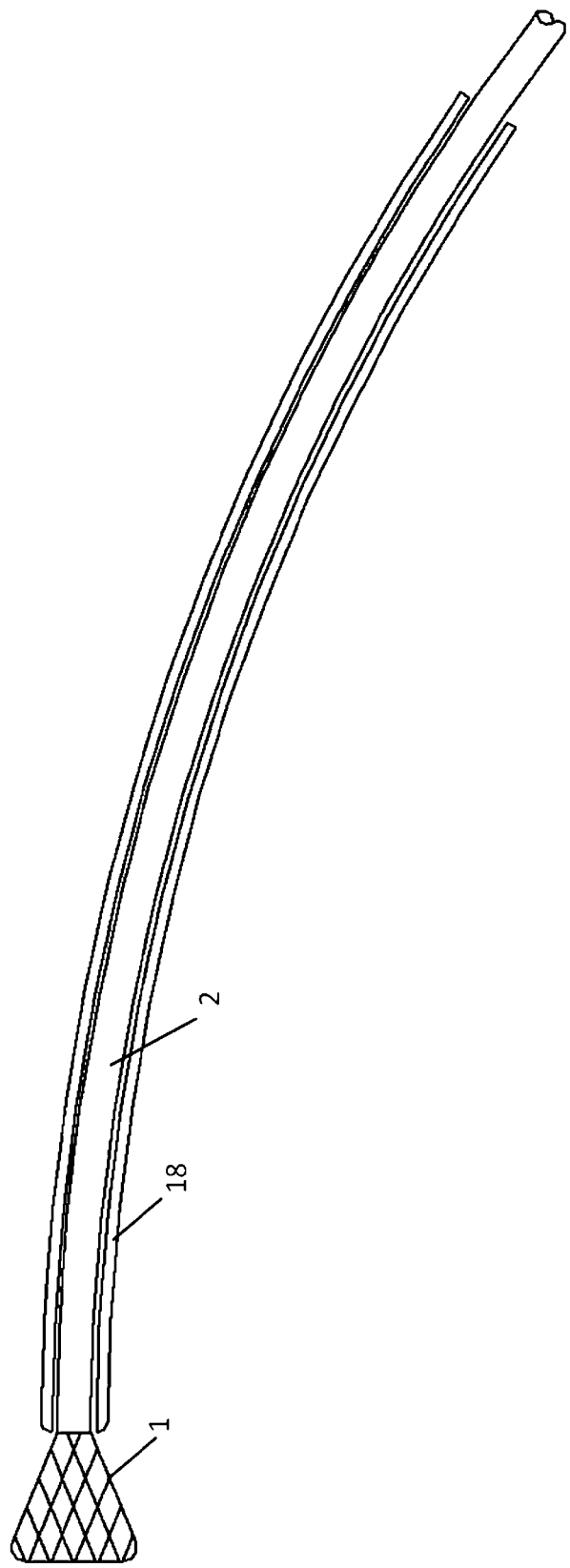

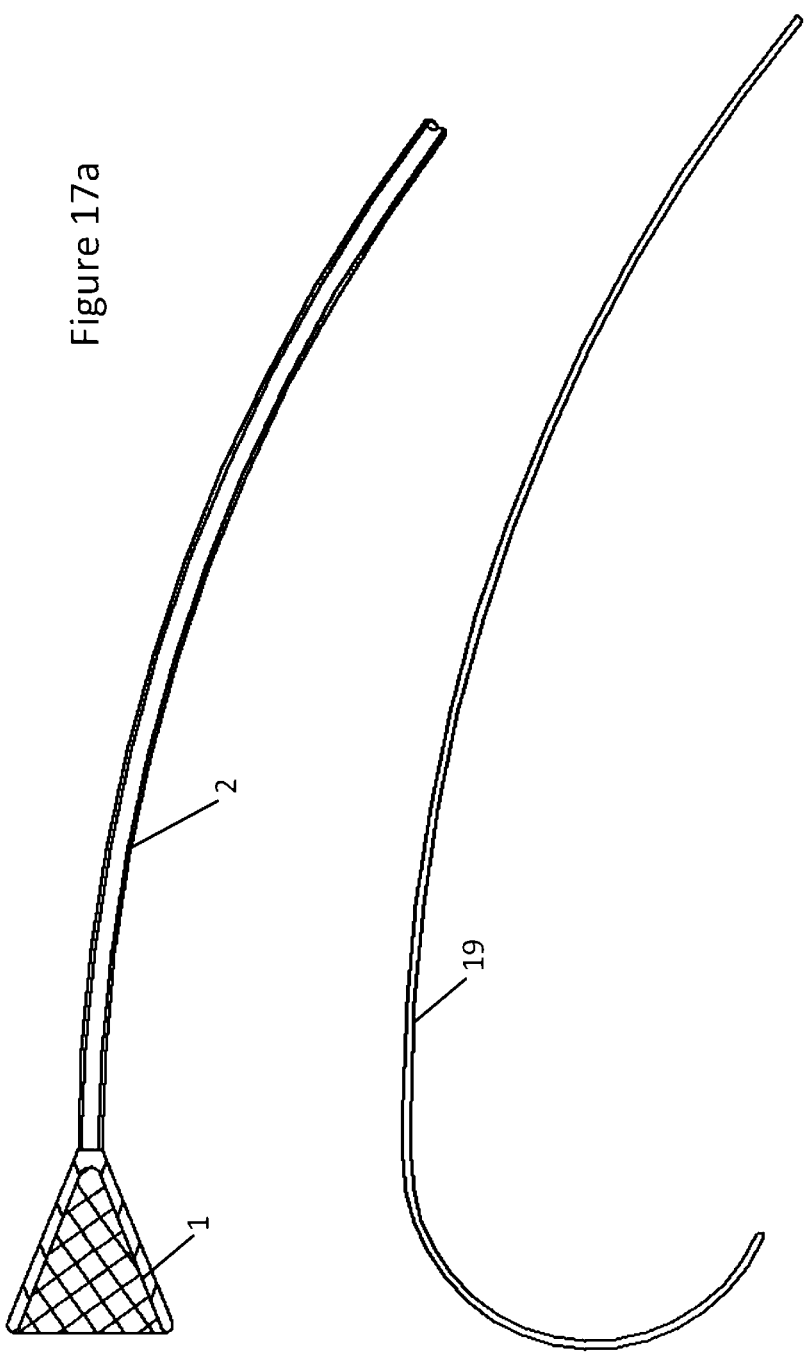

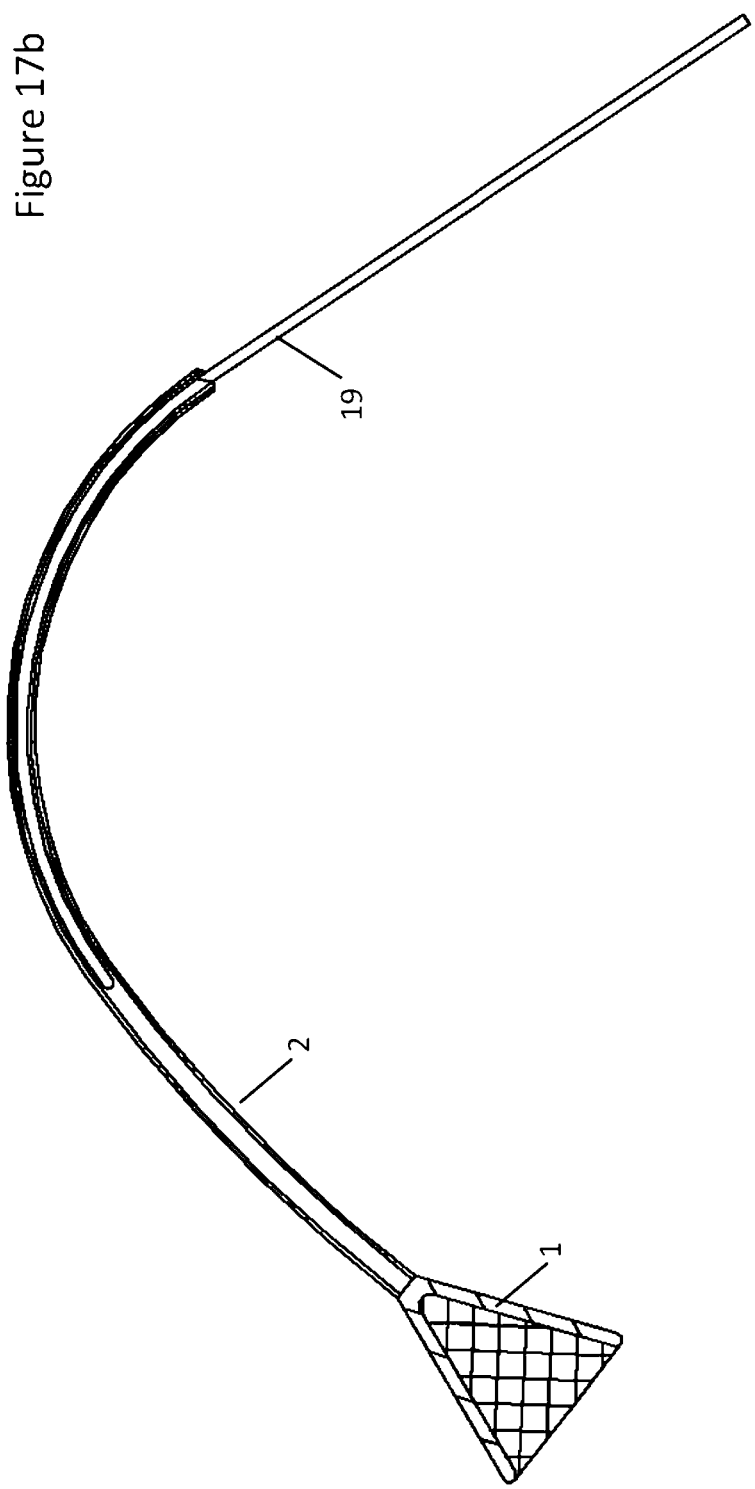

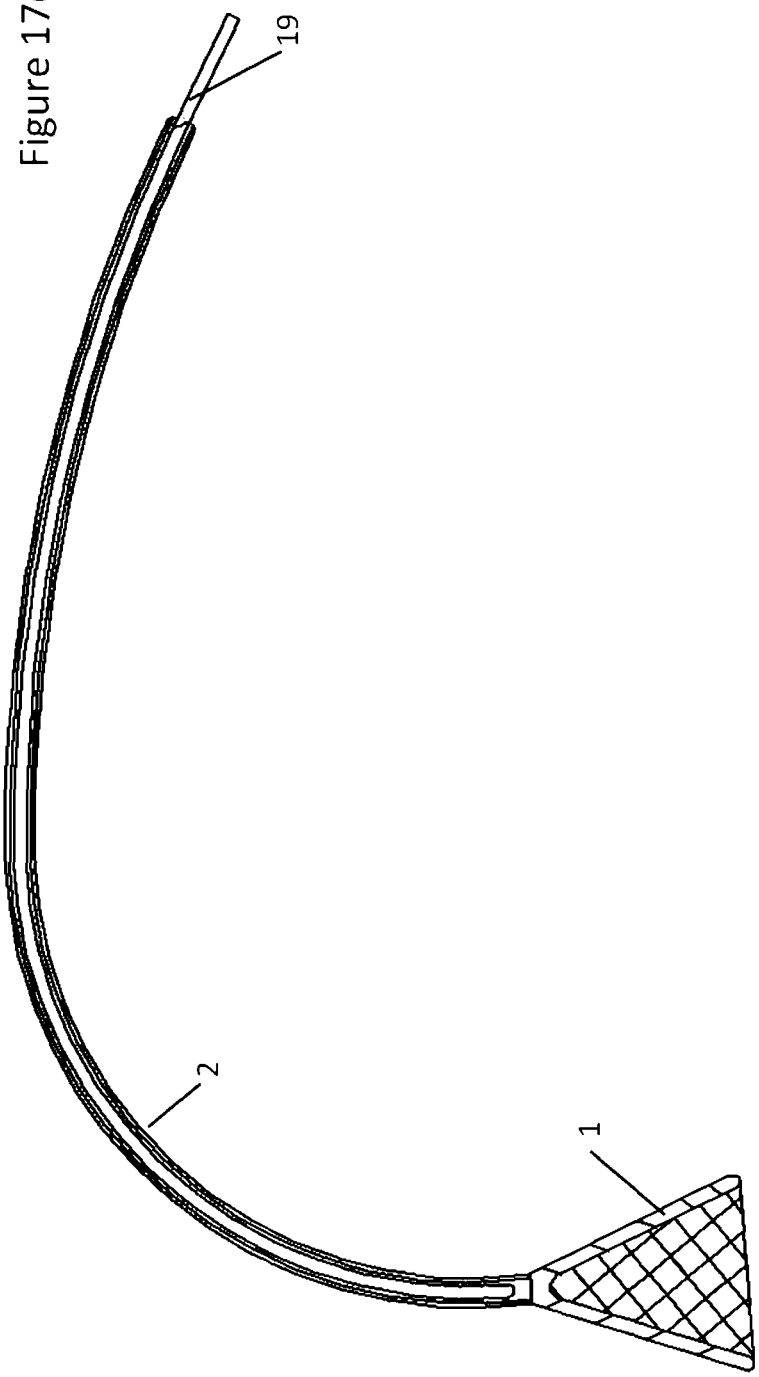

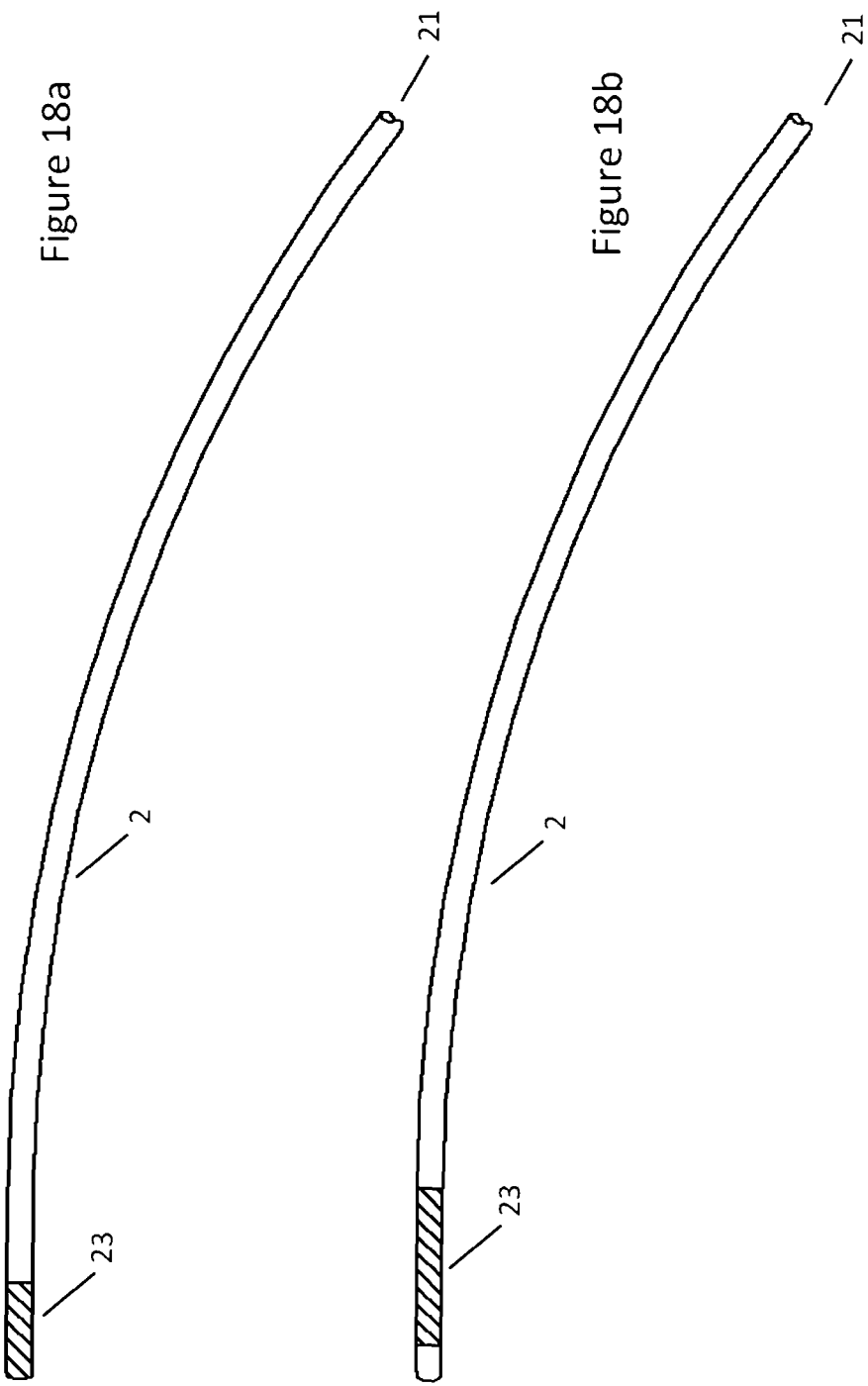

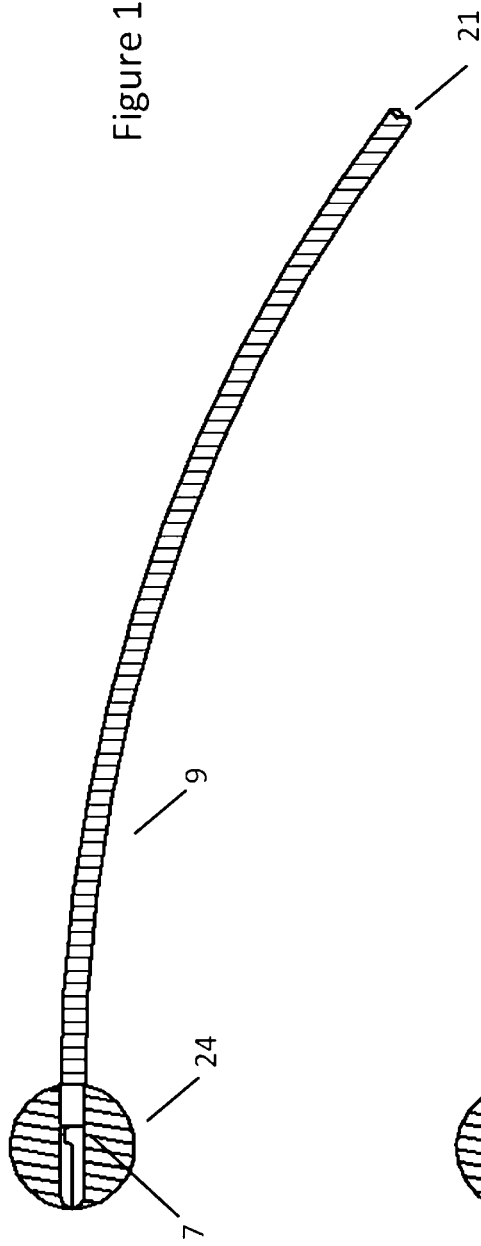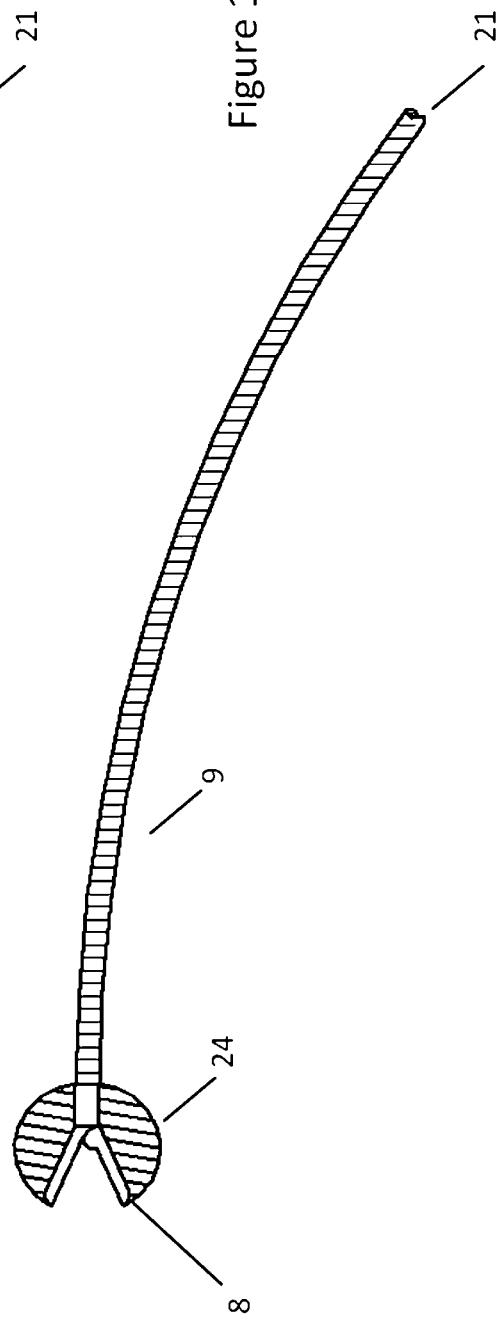

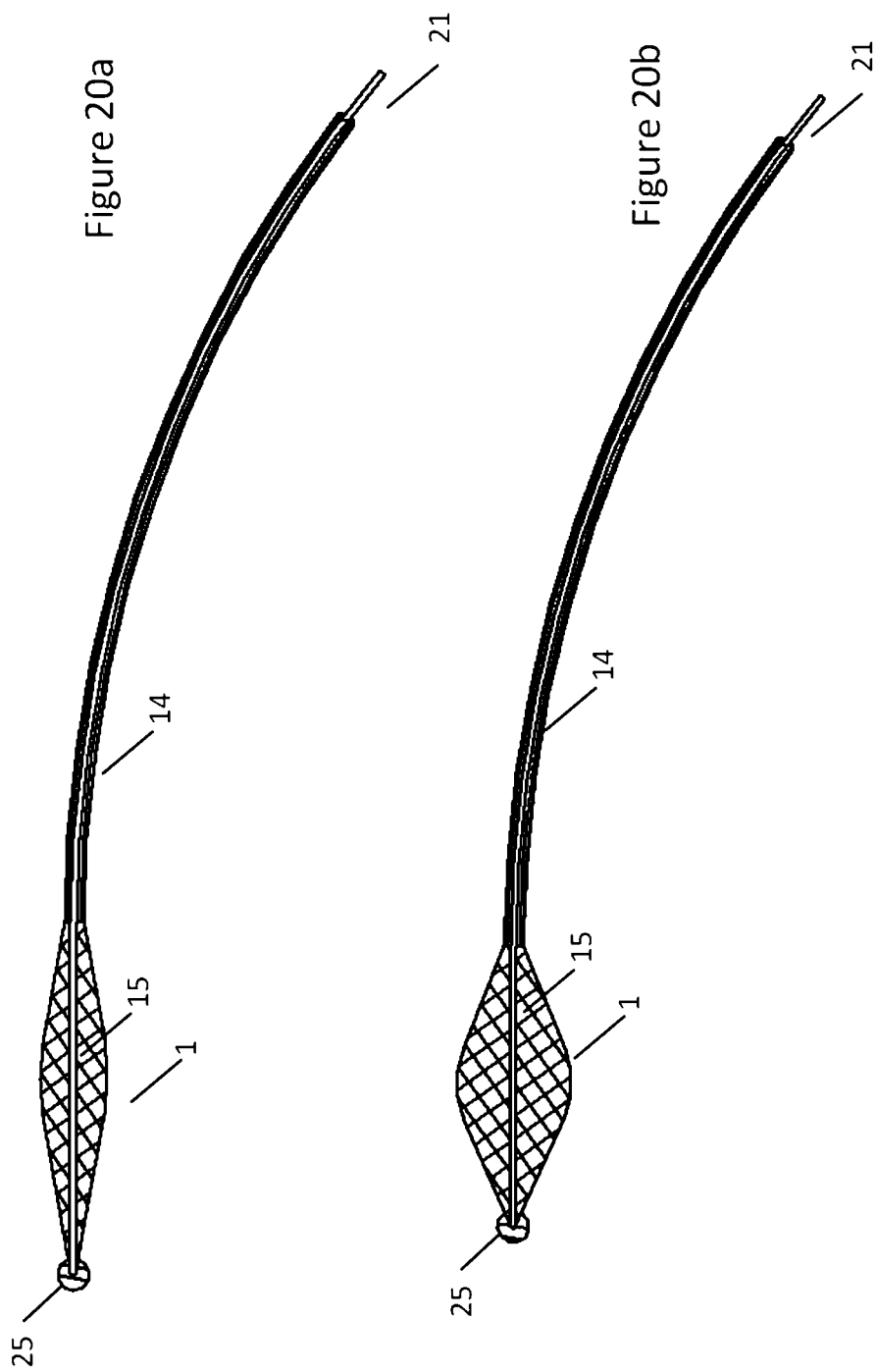

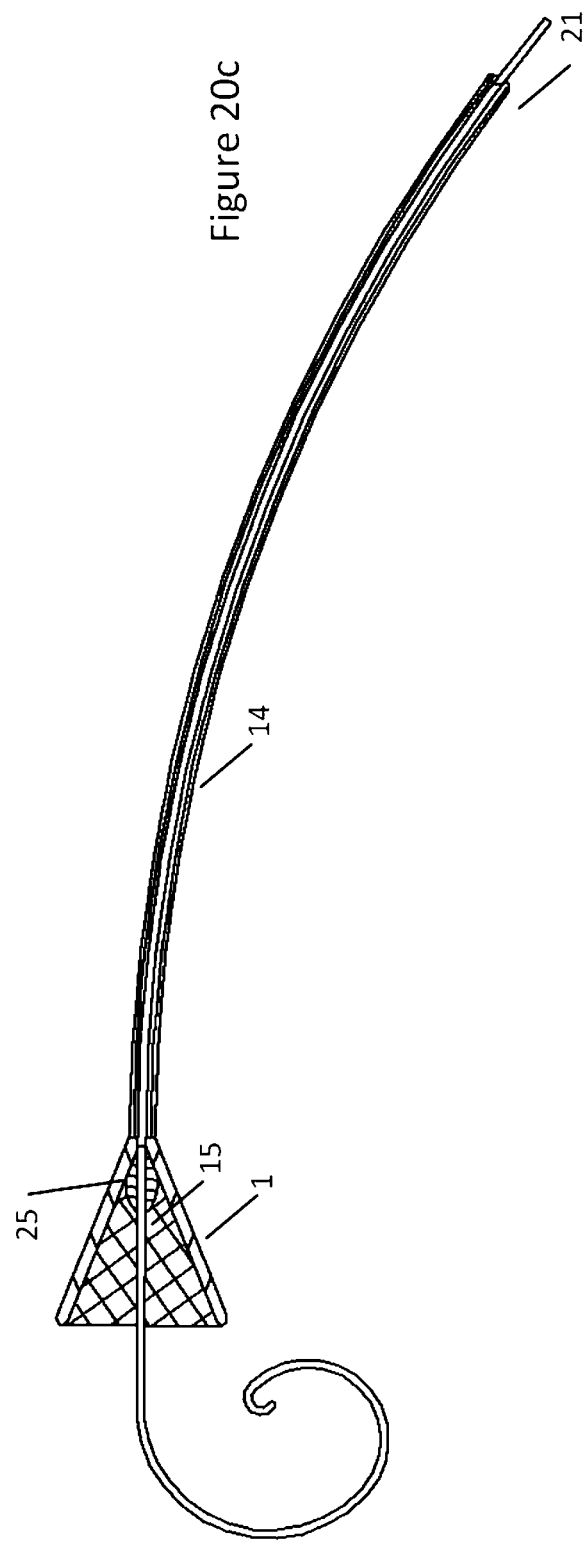

ATRAUMATIC MEDICAL DEVICE

RELATED APPLICATIONS

This application claims priority to U.S. Provisional Application Ser. No. 61/891,797 filed Oct. 16, 2013 entitled Atraumatic Medical Device, which is hereby incorporated herein by reference in its entirety.

BACKGROUND

Field of Invention

The present invention relates to systems and methods to enable medical device delivery into a patient's body, more particularly to systems and methods to protect tissue from injury during manipulation or after implantation of medical devices.

Description of Related Art

Devices such as catheters and leads have long been used in medicine to position within various organs or cavities in the body. Some of these devices cause trauma to the adjacent tissue with which they make contact due to the force with which they are advanced or placed, causing complications and poor outcomes. Perforation of organs by these catheters and probes causes significant morbidity and mortality. Soft material positioned at catheter tips is sometimes used to minimize tissue disruption by the tips of devices. These tips have improved safety, but they provide little spring force or distribution of the loads applied by catheter advancement. In addition, there are cases in which the catheter tips are intentionally applied against tissue, but there is little to no user feedback regarding the amount of applied force at the tip or the proximity of the tip to the tissue with which it is in contact. Additionally, the tips are non-conductive and so are not useful for applications such as cardiac rhythm management or tissue signal recordings.

For example cardiac pacemaker and defibrillator leads are positioned on a temporary or long-term basis in patients with heart disease. The contraction of the heart is controlled by specialized tissue that conducts an electrical wave across the heart muscle. That electrical wave controls and coordinates heart muscle contraction. In certain medical conditions, the conduction system of the heart is abnormal, leading to slow or abnormal heart rhythm. Physicians often need to insert catheters into the heart to correct the problem. These catheters have one or more electrical conductors that are connected to a device that generates rhythmic electrical current to control, or pace, the heart contractions. One conductor is usually positioned at the distal tip of the catheter. The catheter is typically inserted into a heart chamber through a blood vessel. The tip of the catheter is usually pushed up against the inside of the heart chamber to place the electrical conductor is contact with the heart tissue. A current is transmitted through the catheter to the heart muscle, pacing the muscle to contract.

One problem with these pacemaker catheters or leads is that they can perforate the heart tissue. To provide electrical contact to the heart muscle, the catheter or lead must be pushed to provide some level of force against the heart muscle. Contraction of the heart muscle against the catheter or lead may cause the catheter or lead to erode through or perforate the muscle wall. Perforation leads to leakage of blood from the heart to the pericardial sac that surrounds the heart. When the pericardial sac fills with blood, the heart is compressed from the outside and cannot fill with blood. This condition is called cardiac tamponade, which untreated often leads to death. Perforation occurs because the force applied to the tip of the catheter pushes the catheter into the muscle, which in places (such as the right ventricle, the left or right atrium, or the apex of the left ventricle) can be quite thin. Similar erosion may occur when catheters or leads are in contact with other organs. Motion or simple continued force may cause erosion or burrowing of the catheter or lead.

These procedures result in complications such as the aforementioned cardiac perforation in up to 2% of the procedures. Several methods have been used in the past to reduce the possibility of tissue trauma. One embodiment includes combining a catheter with an inflatable balloon tip while others use softer catheter tip materials that are less likely to cause trauma. These have their own limitations related to suboptimal stability and potential migration. Migration of a pacer lead, or loss of capture, results in an immediate inability to pace the heart muscle which can be deadly in a patient that requires pacing to ensure adequate rhythm.

Additional difficulties in positioning the catheter include placing it at the exact place needed or preventing its migration due to the poor ability to secure them at the area of need. There are designs and methods that incorporate deflectable catheters to help with positioning and micro screw-in catheters for securing the catheters into the tissue that have been used in various embodiments.

However, these existing methods have various limitations including the risk of poor contact at the required site, risk of trauma leading to organ perforation, migration away from area of implant or being flimsy or difficult to maneuver.

Determination of the position of the catheter or lead relative to the organ is also important in providing proper, safe apposition of the tip to the organ, in particular the completeness of contact and determination of the proper amount of tip pressure. Location, position and orientation of catheters can be determined by a combination of tactile feedback and visual imaging based on fluoroscopy, which require substantial physician judgment based on experience. Fluoroscopic images provide a general sense of location, but verification of the catheter location relative to internal vessel or cavity margins require injections of contrast media to define a two-dimensional picture of the target space. During a complex procedure in which a catheter is intended to be placed against a target site, a number of contrast injections may be necessary to continually verify that positioning remains adequate. These contrast injections can add to patient risk by increasing the demand on the kidneys of the patient, particularly in patients that are already at risk of kidney failure. In extreme cases, this increased load can result in a condition known as contrast induced nephropathy.

Another catheter example is one used in the heart to record the local intracardiac electrical activity (intracardiac electrocardiogram). Similarly, therapeutic catheters used to delivery energy (such as radiofrequency energy to alter cardiac tissue), alter cardiac temperature (such as cryoablation catheters), or image cardiac tissue (such as ultrasound catheters) require precise placement and inappropriate use can perforate the heart muscle. There are also catheters used to procure tissue samples called bioptomes or biopsy forceps. These catheters are used to navigate to a selected target area and cut a small piece of tissue from the target site for examination. During this tissue extraction, excessive force on the catheter during advancement or actuation can also result in perforation. Other catheters are used to provide for stabilization and positioning of puncture needles to facilitate the crossing of membranous tissue such as the intra-atrial septum.

Additionally, there are systems that are used to deliver contrast or therapeutic agents to the vasculature, the heart or another target site in the body that do not have a mechanism to stabilize the system or protect the tissue from damage. Straight guide catheters and pigtail catheters are often used for contrast injection at a location such as the left atrium. In certain locations, the left atrial wall can be as thin as 0.5 mm between the pectinate muscles which would make it susceptible to perforation or damage during a high-velocity contrast injection if the catheter orifice is too close to the atrial wall when the injection is performed. Similarly, needles are often used to inject stem cells into the wall of the left ventricle with little control over catheter tip position, relying on physician skill to stabilize the catheter tip position during the procedure.

While catheterization is often performed in order to access the vasculature and the cardiac anatomy, it is understood that similar devices are used in a number of other locations within the body. The use of and risks associated with the existing technology as described above certainly apply to these other areas as well, including but not limited to bladder examinations and biopsy, colonoscopy procedures and biopsy, and general endoscopic surgical procedures.

A device that can provide improved tactile or visual feedback related to system proximity to target tissues, as well as catheter tip stabilization and approximation of an expandable surface to distribute the tip apposition force imparted by the catheter across a greater surface area in order to reduce focal pressure would ultimately result in safer system use, reduced patient risk and better patient outcomes.

SUMMARY

The object of the invention is to propose an atraumatic design by using a catheter with an atraumatic tip that compresses and provides some visible displacement and spring force under load, acting as a shock-absorber or bumper. The stiffness of the atraumatic tip is less stiff than the body of the catheter so that forces applied through advancement of the stiffer catheter body are not necessarily translated directly to tissues with which the tip comes in contact. The atraumatic tip could include any number of conductive or nonconductive materials (like a fabric mesh, metal, alloy components, polymer or foam rubber, plastics, ceramics, gels, etc.). The tip can be designed to make use of superelastic materials such as nitinol in order to allow for large deformations without plastically deforming the material. Alternately, the tip can be designed such that the deformations do not exceed the elastic properties of the chosen material during normal use so that superelastic material properties are not necessary. Some examples of these typically elastic materials are foam polymers, polymeric fibers and stainless steel wire. The tip will minimize trauma from repetitive organ motion, catheter motion or from sudden forces from events like coughing, valsalva or positional changes by reducing the forces transmitted between the target tissue and the catheter by allowing for translation between the two with minimal increase in force. The atraumatic tip can be mounted permanently at the tip of the catheter or mounted in a way that it can slide or be released to take the optimal tip position to offer tissue protection after insertion into the body.

The tip can be designed to be expandable such that the surface area of the tip during use is substantially greater than the surface area of the tip during passage through the vascular access site. This increased surface area distributes the forces applied to the device across a broader surface area than the device in the collapsed configuration, reducing the pressure that is focally applied at any one contact point within the body. The increased surface area of the tip can also be used to increase the surface area of an applied therapy. The configuration of the tip design can be cylindrical, conical, spherical or of a more complex geometry such as circumferentially ribbed in order to provide the preferred performance under a given load or displacement. The tip can be constructed in a filled solid form such as a compressible foam-filled cylinder or can be a shell such as a hollow cone constructed of nitinol mesh. In one embodiment, a foam cylinder embedded with conductive or magnetic particles or fibers is mounted to the catheter tip in such a way that the tip can be radially compressed to fit into a catheter diameter smaller than that of the deployed tip configuration. In another embodiment, a hollow cone built with an overlapping mesh braid provides the physical configuration preferred for device function while also providing improved column strength relative to the strength of a single layer of mesh and managing the loose braid ends by incorporating them back into the body of the catheter so that the tissue contact surface of the cone is a folded edge of the mesh. The distal end of the tip may have a barb or other means by which to affix to tissue at the target site. This will prevent movement of the distal electrode, while the soft component at or near the distal end acts as a shock absorber to prevent any distally directed force from applying a potentially damaging compression to the target site. It may also prevent a proximally directed force from applying a tensile force to the site and risk dislodging the electrode from the tissue.

It is another object of the invention that the distal tip can provide one or multiple feedback mechanisms to the operator to guide safer insertion and enable additional maneuvers as needed. The feedback loops envisioned with this device include a visual feedback based on the visual identification of change in shape of the distal tip or the shaft of the catheter (such as under fluoroscopy or other imaging methods). For example, in one rendition of this feedback loop, the distal tip is expected to have a collapsible mesh, which on contact with a surface collapses along an expected range proportionate to the pressure applied. This will allow the operator to be sure that the distal tip is making contact with the tissue of interest.

Another feedback mechanism entails tactile feedback to the operator as the spring tip collapses, stretches or deforms based on the tip resistance encountered when contact is made with the tissue of interest.

Yet another mechanism relates to feedback from displacement sensors placed in the device tip or shaft where the absolute or relative displacement of sensors provides feedback to the operator about the location of the tip, pressure on the tip or the presence of or loss of contact with the catheter. Embodiments with pressure/touch based auditory or visual signals based on preset values are envisioned. In one version, a simple series of radiopaque markers would allow the operator to observe compression on x-ray or ultrasound imaging.

In one embodiment, the catheter will have electrodes incorporated into the spring tip and along the shaft to transmit electrical impulses. Alternately, the spring tip itself can be constructed from a conductive material and be the electrode itself.

Alternately, the catheter can be configured to additionally receive electrical impulses in order to act as a sensor in order to provide feedback relative to patient conduction in an intracardiac electrocardiogram.

In yet another embodiment, the electrode on the spring tip can be used to impart energy in such a way in that it alters the temperature of the target tissue. RF ablation can be performed by using radiofrequency transmitted through the catheter to heat the target site.

In another embodiment, cryoablation can be performed more reliably by incorporating the atraumatic tip on the end of the cryoablation catheter in order to ensure appropriate contact between the catheter and the target site during the cryoablation procedure.

The soft distal end of the device may also be used in an array, in which there are multiple device tips included in single construct. Such an array may be useful for mapping electrical activity in cardiac tissue, as well as selective ablation of electrical pathways, and the soft tips would provide for continuous contact with the target sites while preventing the application of excessive force.

Alternately, the spring tip may be used with a device such as an ultrasound catheter in order to provide visual feedback on fluoroscopy as to position relative to proximate anatomic structures, and to reduce the risk that the tip of the ultrasound catheter could cause damage during insertion and manipulation.

In another embodiment, this invention is envisioned to enable certain applications that require taking tissue samples where in the atraumatic distal tip acts like a bumper and protects the tissue from injury until the stiffer tissue sampler (like a bioptome) is allowed to make contact with the tissue of interest. The spring tip can also be incorporated into a method where the bioptome is activated to take a tissue sample after a predetermined range of displacement is noted based on visual or sensor based feedback after appropriate tissue contact is confirmed.

Alternately, a catheter with the spring tip can be used as the conduit for passage of a bioptome. The catheter can be placed in the preferred position at the surface of the target tissue, using the visual feedback from the deformation of the spring tip to indicate location relative to the target site. The bioptome is then passed through the catheter to the target site and the tissue sample is obtained. This can be particularly useful if multiple tissue samples are desired, as the catheter may remain in position while the bioptome is being passed in and out of the vasculature, ensuring that the location of the tissue sampling is well controlled.

In another embodiment, this invention is envisioned to enable certain applications that require tissue puncturing wherein the atraumatic distal tip acts as a bumper and protects the tissue from injury during system advancement and localization. Once the site of desired puncture is confirmed, the atraumatic distal tip allows the sharp puncturing needle or device to be exposed. The spring tip is also expected to anchor the puncture apparatus by providing broad tissue contact and stability to direct the puncturing tip. The spring tip can also be incorporated into a method where the puncturing tip is activated after a predetermined range of displacement is noted based on visual or sensor based feedback once appropriate tissue contact is confirmed. This tissue puncture may be used for passage of a puncture needle through membranous tissue such as the intra-atrial septum, or could be used for the local injection of a therapeutic agent such as stem cells to a target site.

Yet another embodiment of the invention is to protect fragile tissues during high volume or high pressure injections of fluid. In the case of an injection of contrast or other diagnostic agent into the left atrium, the injection is often performed through a guide catheter or pigtail catheter. If the tip of the catheter is too close to a fragile location in the left atrium, there is risk that the injection could damage or perforate the left atrial wall. The invention can provide visual feedback as to the location of the catheter tip relative to the wall, as well as potentially be designed to act as a limiter to prevent misplacement of the catheter tip by acting as a stand-off relative to the wall at a fixed displacement.

Another aspect of the invention relates to the continued tissue protection offered by the atraumatic spring tip in addition to helping with atraumatic initial placement when the device is left in the body for an interval of time. The shock-absorbing tip will minimize trauma from repetitive organ motion or catheter motion or from sudden forces from events like coughing, valsalva or positional changes.

In other embodiments to enable placement or improve maneuverability, the shaft of the catheter may have a segment that could be reinforced when needed with a flexible, shapeable or pre-shaped retractable stylet or by filling an injectable chamber in the shaft to modify rigidity of the catheter to allow maneuverability and directional control.

Yet another aspect of the invention features the incorporation of temporary or permanent placement of materials with magnetic properties that will allow deflecting or directing the catheter for easier placement and securing at the area needed. In embodiments where magnetic materials are used an external magnetic field can be used to move or direct the catheter as well as secure it to a location.

In another embodiment, the atraumatic tip can be combined with an inflatable balloon to help with flow directed placement or inject materials into the balloon to increase surface area of contact with the tissue or allow for injection of materials with magnetic properties which, when combined with an external magnetic field would allow catheter placement or securing to a site while minimizing dislodgement.

The catheter shaft could allow the insertion of additional catheters if needed and may have an injectable lumen to deliver fluids or drugs. This catheter shaft can have an open inner lumen that is configured to be compatible with a guidewire such that placement of the catheter within the target site is facilitated by advancement over a cardiac guidewire.

Alternatively, in order to facilitate device insertion into the vasculature through a vascular introducer, the spring tip can be manufactured in such a way that the distal tip can be elongated by actuation. Elongation of the distal tip is enabled by advancing an inner member attached to the distal end of the spring tip material relative to the outer catheter that is attached to the proximal end of the spring tip material. This would protect the tip as the device passes through a hemostatic seal in the vascular introducer and through the vessels or chambers of the body, yet allow for actuation of the device into the desired configuration prior to engaging the distal tip with tissue at the target site.

In another embodiment, the mechanism for reducing the risk of trauma associated from the use of the device is to add a spring or shock-absorbing member behind the catheter tip itself or in the body of the catheter. This mechanism allows a catheter tip to function in its typical manner while providing a means of displacement absorption in the catheter without the application of significant additional force against a target site within the vasculature or cardiac structure. Additionally, this mechanism can be configured as a series of spring members within the catheter shaft, with sequential spring members being engaged as the forces applied to the catheter tip increased.

BRIEF DESCRIPTION OF THE DRAWINGS

FIG. 1a is a side view of an embodiment of a distal end portion of a shock absorbing bumper tip;

FIG. 1b is a side view of an embodiment of a distal end portion of a shock absorbing bumper tip;

FIG. 2a is a side view of an embodiment of a distal end portion of a shock absorbing bumper tip partially collapsed due to tip pressure;

FIG. 2b is a side view of an embodiment of a distal end portion of a shock absorbing bumper tip partially collapsed due to tip pressure FIG. 3a is a side view of an embodiment of a distal end portion of a shock absorbing bumper tip in which an electrode is built into the catheter tip and exposed when the mesh is in contact with the target tissue;

FIG. 3b is a side view of an embodiment of a distal end portion of a shock absorbing bumper tip in which an electrode is built into the catheter tip and exposed when the foam is in contact with the target tissue;

FIG. 4b is a side view of an embodiment of a distal end portion of a shock absorbing bumper tip;

FIG. 5 illustrates the use of an embodiment of a device with a spring tip being used to take an intracardiac electrocardiogram;

FIG. 6a is a side view of an embodiment of a distal portion of a shock absorbing bumper tip on an ultrasound catheter;

FIG. 6b demonstrates the embodiment of FIG. 6a protecting tissue from trauma from the catheter tip during use in the cardiovascular anatomy;

FIG. 7a is a side view of an embodiment of a distal portion of a shock absorbing bumper tip on a bioptome in a closed configuration;

FIG. 7b is a side view of an embodiment of a distal portion of a shock absorbing bumper tip on a bioptome in an open configuration;

FIG. 8a is a side cutaway view of an embodiment of a conical foam spring tip used in conjunction with a bioptome in a closed configuration;

FIG. 8b is a side cutaway view of an embodiment of a conical foam spring tip used in conjunction with a bioptome in an open, compressed configuration;

FIG. 9a is a side cutaway view of an embodiment of a spring tip, providing a conduit for any one of a multitude of tools to be used in conjunction with a device;

FIG. 9b is a side cutaway view of an embodiment of a conical foam spring tip used in conjunction with a bioptome in an open, compressed configuration;

FIG. 10 is a side view of an embodiment of a distal portion of a shock absorbing bumper tip on a needle;

FIG. 11 is a side view of an embodiment of a distal portion of a shock absorbing bumper tip on a needle where the spring tip collapses and the sharp tip is exposed to puncture tissue at a desired location;

FIG. 12b illustrates how an embodiment of a spring tip on an open catheter is used to prevent the catheter from sitting against tissue during a contrast injection to protect the tissue during a high-pressure injection;

FIG. 13a is an embodiment of a mechanically actuated spring tip of the invention in an elongated configuration;

FIG. 13b is an embodiment of a mechanically actuated spring tip of the invention in partially actuated configuration;

FIG. 13c is an embodiment of a mechanically actuated spring tip of the invention in a treatment configuration;

FIG. 15 is a cross-section of a spring tip pacer embodiment with a lumen that allows for guidewire placement and/or injection of diagnostic or therapeutic agents;

FIG. 16a is a side view of an embodiment of a two-piece device having an outer sheath and inner sheath;

FIG. 16b is a side view of the embodiment of FIG. 16a with a spring tip being deployed;

FIG. 17a is an embodiment of a kit including a device of the invention and a shaped stylet that may be advanced or retracted within the device as necessary to adapt the orientation of the distal end of the device to allow for navigation or placement;

FIG. 17b is a cross section of the assembled kit of FIG. 17a showing how the catheter shape is modified by the insertion of the relatively stiffer stylet;

FIG. 17c is a cross section of the assembled kit of FIG. 17a showing illustrates the continued shape modification of the catheter as the curved stylet is advanced to the distal end of the spring tip catheter;

FIG. 18a is a side view of an embodiment of a device including a spring tip catheter that allows for compression axially, but is not designed to expand circumferentially except under compressive load;

FIG. 18b is a side view of an embodiment of a device having a spring member located proximal of the distal tip of a catheter shaft in order to provide a shock-absorbing capability without affecting the geometry or configuration of the distal tip itself;

FIG. 19a is a side view of an embodiment of a device of the invention having an atraumatic bioptome tip in a closed configuration;

FIG. 19b is a side view of the embodiment of FIG. 19a in an open configuration;

FIG. 20a is a side cross section of an embodiment of a device of the invention having a foam atraumatic tip used in conjunction with a mesh, mechanically activated tip;

FIG. 20b is a side cross section of the device of FIG. 20a in a partially activated configuration; and FIG. 20c is a side cross section of the device of FIG. 20a in a fully activated configuration.

DETAILED DESCRIPTION OF THE INVENTION

Figure 4A:
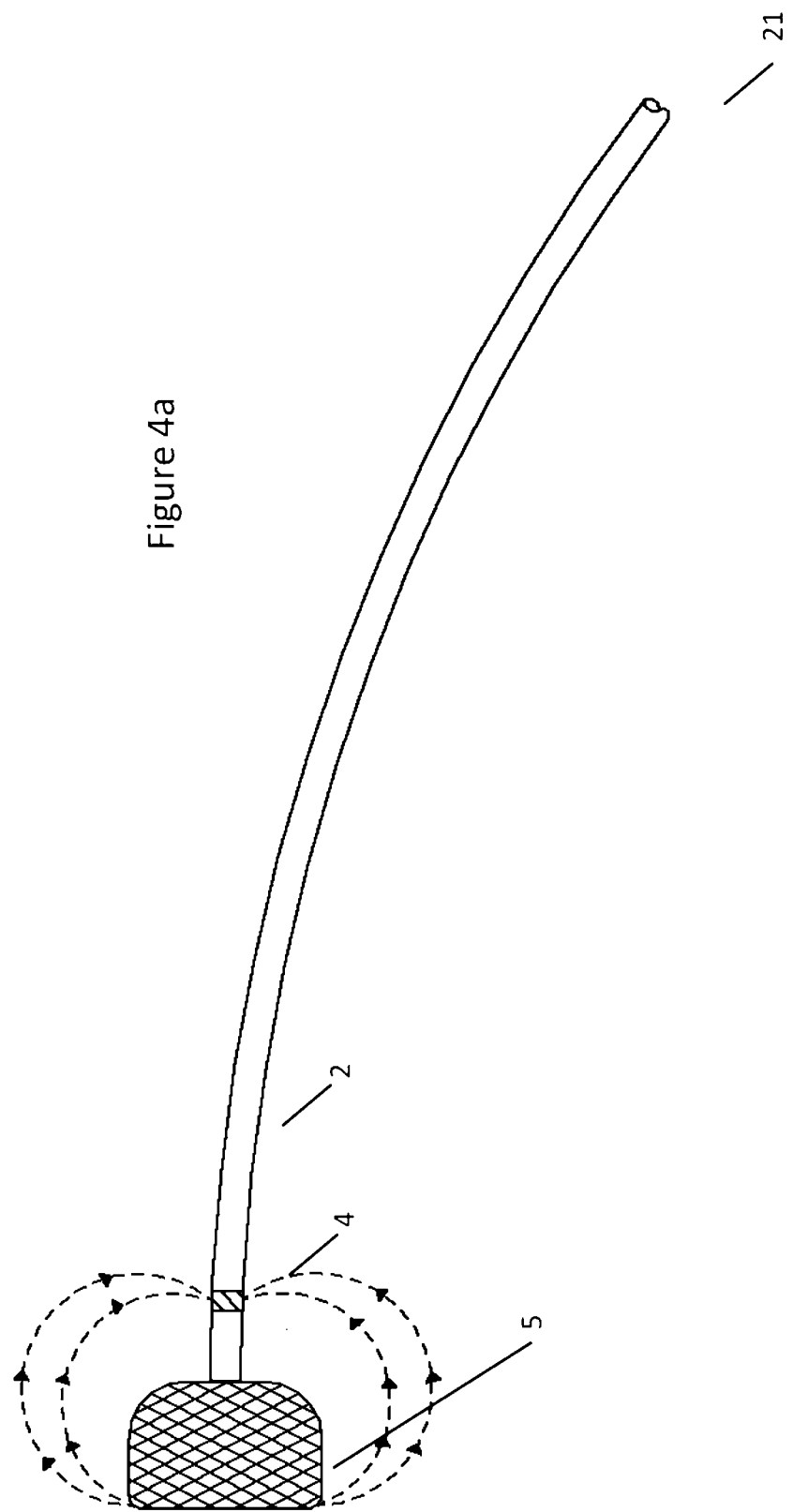
FIG. 4a is a side view of an embodiment of a distal end portion of a shock absorbing bumper tip.

Turning now to the Figures, and first to FIG. 1, there is shown an embodiment of an atraumatic medical device of the invention. The device generally includes a catheter 2 and a spring tip 1 attached to the distal end of the catheter 2. In a relaxed state without contact against tissues or other structures within the body, the mesh spring tip 1 expands upon deployment through a catheter and takes a conical shape. In this embodiment, the tip is demonstrated as a mesh or braid, but can be manufactured from mesh, braid, foam, gel, an inflatable device such as a balloon, or any one of a number of metallic or polymeric materials that can expand upon exit from a delivery catheter while being flexible enough to reduce contact forces against tissues or body structures. An example of a device built with foam is demonstrated in FIG. 1b. The cylindrical foam spring tip 23 is attached to the distal end of catheter 2.

When the device is inserted into the vasculature of the body, the distal end of the catheter 2 containing the spring tip 1, 23 may intentionally or unintentionally contact tissues or other structures. An intended response of the spring tip to contact with these structures is demonstrated in FIGS. 2a and 2b. In FIG. 2a, the conical mesh spring tip 1 distorts under an axial load placed on the distal end of the catheter 2, visually deforming into a more cylindrical shape. In FIG. 2b, the cylindrical foam spring tip 23 compresses axially and widens in diameter under a load placed on the distal tip 20. These deformations provide the device operator the opportunity to observe the contact using fluoroscopy, distributing the load across a greater surface area than a tip without the spring feature, preventing additional force from being applied by the device and potential damage to the tissue with which contact has been made.

FIG. 3a shows an embodiment in which the mesh spring tip 1 is used on a temporary pacing catheter 2. In a conical state, a distal electrode 3 or cathode 4 of the pacing catheter 2 is shielded from contact with the target tissue by the conical shape of the spring tip 1. In the image shown in FIG. 3a, contact has been initiated with the target tissue (not shown), resulting in a cylindrical spring tip and an exposed distal electrode 3. By running an electrical current from the proximal end 21 through the pacing catheter 2 of FIG. 3a, current flows from the distal electrode 3 into the target tissue, and returns via the proximal electrode 4, or anode.

Similarly, the embodiment shown in FIG. 3b demonstrates a foam tip 23 utilized in a similar manner. The foam tip 23 shields the electrode tip 3 when no axial load has been applied, while the application of force results in compression of the foam tip 23, an exposure of the electrode tip 3 and contact of the electrode with the target tissue.

In an alternate embodiment shown in FIG. 4a, a conductive mesh spring tip 5 serves as the distal electrode. A conduction pathway is created through the catheter 2 in which the electrical current applied from the proximal end 21 of the system is sent through the conductive mesh tip 5. A proximal electrode 4 is placed on the catheter 2 for return current. In each of these pacing embodiments, the anode and cathode can be connected to the proximal end 21 of the system using insulated wires running through a lumen of the catheter 2, one or both of the electrodes can be placed in independent lumens of the catheter 2, or one or both of the electrodes can receive current conducted through a metallic braid, coil or linear filament interposed between layers of the catheter wall. FIG. 4b demonstrates a similar design in which the spring tip is a foam cylinder 23 constructed of a conductive material, or which has conductive particles or filaments embedded within.

FIG. 5 demonstrates the placement of a device with a conductive spring tip 5. The catheter 2 with the distal conductive spring tip 5 is placed through the jugular vein through the superior vena cava and right atrium into the right ventricle. This device is placed against the wall of the right ventricle, and can be used to pace the heart, or to sense electrical impulses for the purposes of generating an intracardiac electrocardiogram.

FIG. 6a demonstrates the spring tip 2 on an intracardiac ultrasound catheter. The spring tip is attached to the ultrasound catheter 22, which limits the ultrasound catheter tip 6 from contact with tissues and provides visual evidence of contact that does occur. FIG. 6b demonstrates the placement of the ultrasound catheter 22 within the aorta, demonstrating the use of the spring tip 1 in the vasculature.

Another embodiment for use of the spring tip is demonstrated in FIGS. 7a and 7b. In this instance, the mesh spring tip 1 is applied to the distal end of a biopsy forceps device. In one orientation, the spring tip 1 remains in the conical or otherwise relaxed state, fully covering the closed jaws 7 of the biopsy forceps. FIG. 7b demonstrates the spring tip 1 coming into contact with the target tissue to be sampled. The spring tip 1 retracts into a cylindrical or otherwise compressed state, exposing the jaws of the biopsy forceps and allowing the jaws to open 8 to contact the tissue and cut a sample.

Similarly, another embodiment for use of the spring tip is demonstrated in FIGS. 8a and 8b. In this instance, a conical foam spring tip 24 is applied to the distal end of a biopsy forceps device. In a first orientation shown in FIG. 8a, the foam spring tip 24 remains in the conical or otherwise relaxed state, fully covering the closed jaws 7 of the biopsy forces while leaving an open channel 25 from the closed jaws 7 to the distal end 20. FIG. 8b demonstrates the conical foam spring tip 24 coming into contact with the target tissue to be sampled. The foam spring tip 24 retracts into a compressed state, exposing the jaws of the biopsy forceps and allowing the jaws to open 8 to contact the tissue and cut a sample.

An alternative to the design demonstrated in FIG. 7 and FIG. 8 is shown in FIGS. 9a and 9b. In this embodiment, the spring tip 1 is connected at a distal end of a catheter 10 that acts as a conduit for a second device. This second device may be a biopsy forceps as shown in this Figure, or alternately any one of a range of devices such as a pacing lead, a puncture needle, a diagnostic catheter or other devices used in the body for diagnostic or therapeutic purposes. FIG. 9a demonstrates a biopsy forceps being advanced from the proximal end 21 with the forceps jaws 7 in the closed orientation. Advancement of the biopsy forceps catheter 9 may be paused while the jaws 7 remain behind the spring tip 1 in order to ensure accurate catheter placement. FIG. 9b demonstrates advancement of the spring tip 1 against a structure, initiating a shape-change in the tip to indicate contact. The biopsy jaws are opened 8 as they progress past the spring tip 1 in order to sample the target tissue. A benefit of using a system that contains the spring tip 1 on an introducer or catheter that acts as a conduit for secondary tools is that the tools can be interchanged at will while maintaining the spring tip 1 position against the target site within the patient.

Another device that can utilize a spring tip is a trans-septal puncture needle. FIG. 10 demonstrates the use of the spring tip 1 on a needle catheter 12 carrying a puncture needle 11. The tip of the puncture needle 11 is shielded by the spring tip 1 until contact is made with the target site. When contact at the correct location is verified, the catheter is advanced to compress the spring tip 1 as shown in FIG. 11 and the tip of the puncture needle 11 is passed through the target tissue.

Figure 12A:
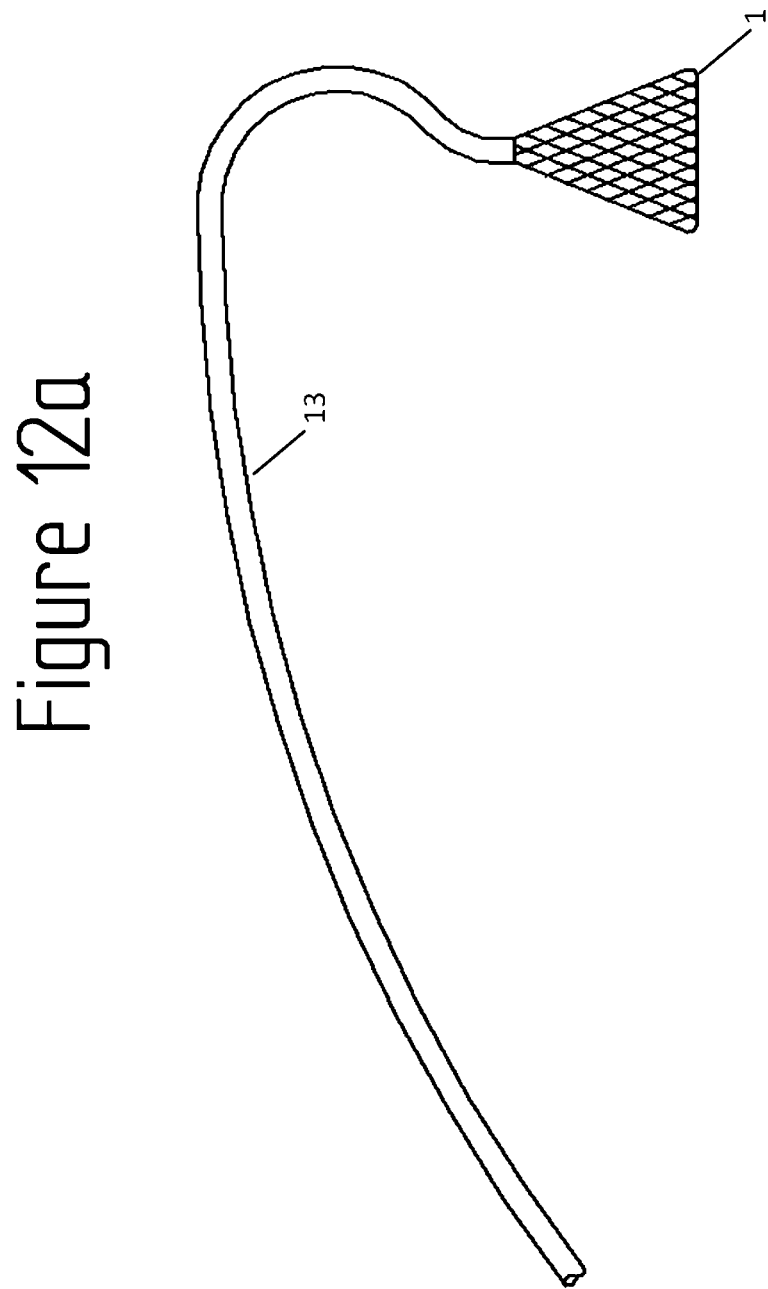
FIG. 12a is a side view of an embodiment of a distal portion of a shock absorbing bumper tip on distal end of an open-lumen catheter.

FIG. 12a demonstrates a spring tip 1 being added to an end-hole injection or guide catheter 13. FIG. 12b demonstrates the use of this catheter to protect cardiac tissue. The catheter 13 is advanced from a femoral venous approach through the inferior vena cava and into the right atrium. It is passed through a trans-septal puncture site from the right atrium into the left atrium, and the catheter tip is placed in the left atrial appendage. When a contrast injection is made in the left atrial appendage, there is a risk of tissue damage due to a high-velocity jet of contrast agent being injected in close proximity to the thin tissue wall of the appendage. Using the spring tip 1 of the catheter, the proximity of the catheter tip to the appendage wall can be easily verified on fluoroscopy, and the spring tip 1 can be used to act as a stand-off to maintain a safe distance from the end of the catheter to the appendage wall during an injection.

FIG. 13*a* demonstrates another embodiment of a spring tip device. Rather than a self-expanding device that assumes the preferred spring-tip configuration upon release from a constraint such as a catheter, the device of FIG. 13*a* is mechanically actuated into the preferred configuration. FIG. 13*a* shows the device in an elongated form, in which the spring tip 1 is held in a lower profile configuration with the distal end 21 of the spring tip attached to an actuating member 15 that extends throughout the catheter 14 and to the proximal end of the system. FIG. 13*b* demonstrates the changing shape of the spring tip 1 as the actuating member 15 is moved proximally relative to the catheter 14. FIG. 13*c* shows the system in a fully-actuated configuration, with a cut-away view of the spring tip 1 showing the actuating member 15 having been pulled through the spring tip 1 to the tip of the catheter 14.

The spring tip may be made of any one of a number of mechanisms, including mesh, braid, foam, gel, springs, and balloons. These mechanisms may be manufactured from a great number of materials including metals, polymers and others.

Figure 14:
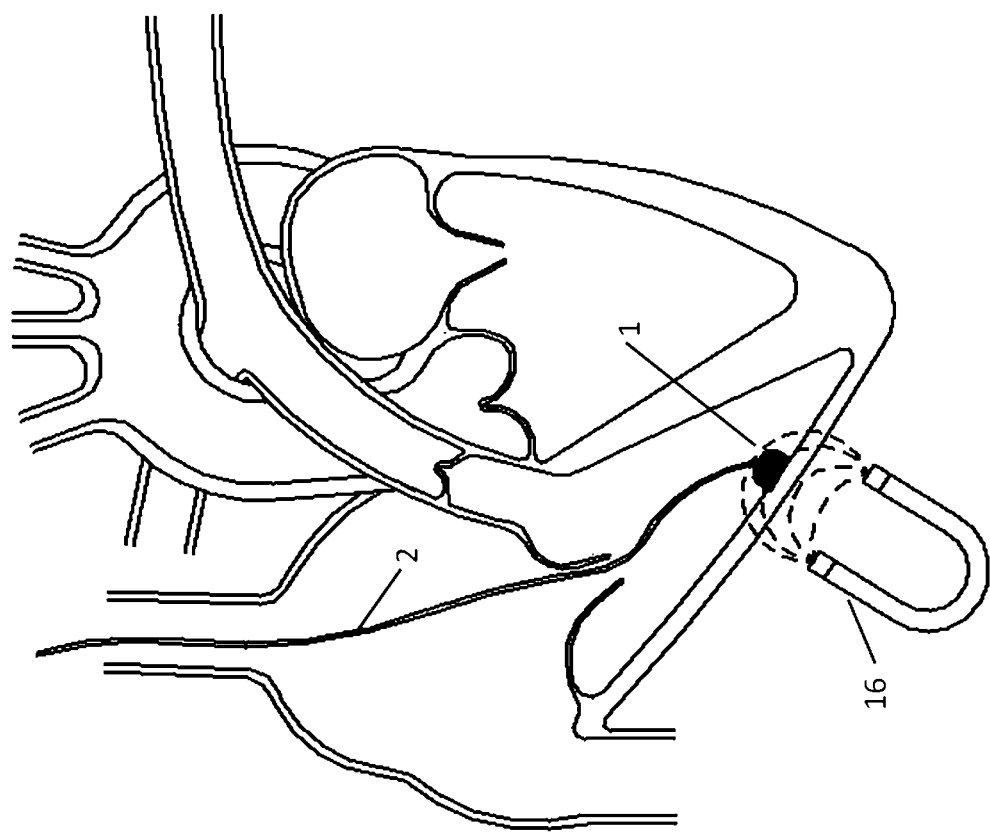
FIG. 14 illustrates an embodiment of a spring tip catheter of the invention with magnetic properties to aid in device orientation and placement.

FIG. 14 demonstrates another potential benefit of the spring tip invention in that the spring tip 1 may be manufactured from a magnetic material such that the tip of the catheter can be manipulated with an external magnet 16 to steer the catheter to a desired location within the anatomy. Additionally, the catheter tip itself can be manufactured with a magnet encapsulated within the tip in order to provide a similar effect.

In another embodiment of the design, as shown in FIG. 15 the device may be manufactured with a lumen through the entire length of the system in order to use secondary devices to aid in placement, diagnosis or therapy. In this cut-away view of the spring tip 1, a guidewire 17 is shown extending from the distal end of the system from the proximal end 21. This lumen can also be used for injecting diagnostic or therapeutic agents or for the placement of other devices.

FIGS. 16*a* and 16*b* demonstrate the expandability of the spring tip 1 in one embodiment. The catheter 2 with the spring tip 1 may be placed into the vasculature through a second catheter or vascular introducer 18. The spring tip 1 is compressible such that it can take on a profile that fits within the introducer 18. Upon advancement from the constraint of the vascular introducer 18, the spring tip 1 expands to a predetermined shape. This expanded shape provides for greater surface area than the diameter of the catheter 2, allowing for distribution of contact forces across a greater area to reduce the pressure exerted by the system against the target tissues. This expanded spring tip 1 also provides for a reduction in applied force due to the flexible nature of the tip. The spring tip 1 can retract and elongate in response to an applied loading cycle, preventing the stiffer catheter from impacting the tissue.

Another embodiment of the invention is the use of a secondary stylet to aid in navigation of the spring tip catheter to reach a target site. FIG. 17*a* demonstrates a catheter 2 with a spring tip 1, alongside a shaped stylet 19. FIG. 17*b* demonstrates the stylet 19 being inserted into a lumen of the catheter 2, and the shape change that takes place with respect to catheter 2 and the orientation of the spring tip 1. FIG. 17*c* demonstrates the stylet 19 being fully inserted into the lumen of the catheter 2, causing further change to the shape of the catheter 2 and the orientation of the spring tip 1. By means of advancing and retracting this shaped stylet 19 in the catheter 2, the shape of the catheter 2 and the orientation of the spring tip 1 may be caused to take on a range of configurations. It is envisioned that a series of stylets with a range of shapes and radii may be swapped into and out of the catheter for use to effect steering of the spring tip catheter.

FIGS. 18*a* and 18*b* demonstrate a device that uses a spring tip catheter that allows for compression axially, but is not designed to expand circumferentially except under compressive load. The spring tip 23 of FIG. 18*a* is located at the distal end of the catheter 2. FIG. 18*b* illustrates the use of the spring member 23 not in the distal tip itself, but rather sits behind the tip in the catheter shaft 2 in order to provide a shock-absorbing capability without affecting the geometry or configuration of the distal tip itself.

The soft portion of the pacer tip may be manufactured into a preformed shape that allows for better adaptation to the target site with which it is designed to contact. In one embodiment, the distal segment 23 of FIG. 18*b* may have a 90 degree bend in order to allow the distal end to lay across a portion of the target site. Additionally, the pacer electrode on the distal end may be designed such that it preferentially contacts the target tissue on the outer surface by increasing the surface area of the electrode on the outer curvature while lessening the contact surface on the inner curvature of the distal bend. This bend may be less than 90 degrees, or could be greater than 90 degrees and include a range of complex shapes to provide the appropriate apposition of the electrode tip to the target site. Additionally, the soft portion of the pacer tip may be malleable so that it can be formed into a shape by the physician just prior to insertion into the vasculature in order to provide a customized fit for the specific clinical application.

FIGS. 19*a* and 19*b* demonstrate another embodiment of the atraumatic bioptome device. In this embodiment of the design, the closed jaws 7 of the bioptome are shielded by a spherical foam component 24 surrounding the bioptome jaws and the entire distal end of the device. As demonstrated in FIG. 19*b*, the foam around the jaws 24 is designed to allow for expansion as the jaws open 8 in order to prevent impingement of jaw function, and to follow the jaws back to a closed configuration to protect surrounding non-target tissues from impact.

FIGS. 20*a*, 20*b* and 20*c* demonstrate how the foam atraumatic tip may be used in conjunction with the mesh atraumatic tip in order to minimize the risk of tissue damage to an even greater extent. The small foam tip 25 can protect the distal end of an actuatable mesh 1 in order to ensure that tissue damage does not occur prior to device actuation.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

We claim:

1. A medical device comprising:
    a catheter having a proximal end and a distal end;
    a spring tip attached to a distal end of the catheter and having a distal diameter greater than a diameter of the catheter when the spring tip is expanded from a single-ply compressed configuration to a two-ply deployed configuration;
    wherein said spring tip is deployed by retracting a distal end of the spring tip proximally until inversion occurs, thereby creating the two-ply deployed configuration and forming a distally-flared cone that is axially compliant such that when a distal end of the spring tip is pressed against a surface, said spring tip compresses axially.

2. The medical device of claim 1 wherein said spring tip comprises a mesh.

3. The medical device of claim 1 wherein said spring tip comprises a foam.

4. The medical device of claim 1 wherein said spring tip comprises an electrode.

5. The medical device of claim 1 wherein said spring tip comprises a cone in a deployed, uncompressed configuration.

6. The medical device of claim 5 wherein said spring tip assumes a cylindrical shape when compressed axially.

7. The medical device of claim 1 wherein said spring tip has a diameter that does not increase when axially compressed.

8. The medical device of claim 1 further comprising a lumen extending through said spring tip and said catheter.

9. A medical device usable to access target tissue comprising:

a first catheter having a lumen;

a deformable spring tip attached to a distal end of said catheter and having a single-ply first configuration, a two-ply second configuration and a third configuration, wherein:

said first configuration is a radially compressed configuration;

said second configuration is a radially expanded configuration created by inverting a distal portion of said spring tip into a proximal portion to form a distally flared cone; and, said third configuration is an axially compressed configuration.

10. The medical device of claim 9 further comprising a second catheter through which the catheter and spring tip are deployed and wherein the spring tip begins to assume the radially expanded configuration from the radially compressed configuration upon exiting the second catheter.

11. The medical device of claim 9 further comprising a mechanism attached to the spring device usable to transform the spring tip between the first and second configurations.

12. The medical device of claim 9 wherein the spring tip has a diameter that increases when the spring tip assumes the third configuration from the second configuration.

13. The medical device of claim 11 wherein the mechanism comprises a distal foam tip.

* * * * *